United States Patent
Yu

(10) Patent No.: US 11,453,688 B2
(45) Date of Patent: *Sep. 27, 2022

(54) PHOSPHORUS IMIDAZOQUINOLINE AMINE DERIVATIVES, PHARMACEUTICAL COMPOSITIONS AND THERAPEUTIC METHODS THEREOF

(71) Applicant: CanWell Biotech Limited, Hong Kong (CN)

(72) Inventor: Ninghui Yu, Wellesley, MA (US)

(73) Assignee: CANWELL BIOTECH LIMITED, Hong Kong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/145,300

(22) Filed: Jan. 9, 2021

(65) Prior Publication Data

US 2021/0253613 A1 Aug. 19, 2021

Related U.S. Application Data

(63) Continuation of application No. 16/980,757, filed as application No. PCT/US2020/015497 on Jan. 28, 2020, now Pat. No. 10,906,923.

(60) Provisional application No. 62/802,260, filed on Feb. 7, 2019.

(51) Int. Cl.
C07F 9/53 (2006.01)

(52) U.S. Cl.
CPC .................. *C07F 9/5325* (2013.01)

(58) Field of Classification Search
CPC ...................................... C07F 9/5325
USPC ........................................ 514/114
See application file for complete search history.

(56) References Cited

PUBLICATIONS

Cancer [online], [retrieved on Jul. 6, 2007] Retrieved from the Internet, URL: http://www.nlm.nih.gov/medlineplus/cancer.html (Year: 2007).*
Lala et al., Role of nitric oxide in tumor progression: Lessons from experimental tumors, Cancer and Metastasis Reviews (1998), 17, 91-106 (Year: 1998).*
Golub et al., Molecular Classification of Cancer: Class Discovery and Class Prediction by Gene Expression Monitoring, Science (1999), vol. 286, 531-537 (Year: 1999).*

* cited by examiner

*Primary Examiner* — Kristin A Vajda
(74) *Attorney, Agent, or Firm* — Milstein Zhang & Wu LLC

(57) ABSTRACT

The invention provides novel phosphorus imidazoquinoline amine derivatives, having agonistic activities to Toll-like receptors (TLRs), in particular TLR7 and/or TLR8, pharmaceutical compositions thereof, and methods of treatment, reduction or prevention of certain diseases or conditions mediated by or associated with TLR7 and/or TLR8, e.g., cancer, graft rejection, autoimmunity, inflammation allergy, asthma, infection, sepsis, and immunodeficiency.

14 Claims, No Drawings

PHOSPHORUS IMIDAZOQUINOLINE AMINE DERIVATIVES, PHARMACEUTICAL COMPOSITIONS AND THERAPEUTIC METHODS THEREOF

PRIORITY CLAIMS AND RELATED APPLICATIONS

This application is a continuation of and claims priority to U.S. Ser. No. 16/980,757, filed Sep. 14, 2020, which is the U.S. national phase of and claims priority to PCT/US2020/015497, filed Jan. 28, 2020, which claims the benefit of priority to U.S. Provisional Application No. 62/802,260, filed Feb. 7, 2019, the content of each of which is incorporated herein by reference in its entirety.

TECHNICAL FIELD OF THE INVENTION

The invention generally relates to novel compounds and therapeutic uses thereof More particularly, the invention provides novel phosphorus imidazoquinoline amine derivatives, having agonistic activities towards Toll-like receptors (TLRs), in particular TLR7 and/or TLR8, pharmaceutical compositions thereof, and methods of treatment, reduction or prevention of certain diseases or conditions mediated by or associated with TLR7 and/or TLR8, e.g. cancer, graft rejection, autoimmunity, inflammation allergy, asthma, infection, sepsis, and immunodeficiency.

BACKGROUND OF THE INVENTION

The immune system is a very diverse system of the host that evolved during evolution to cope with various pathogens present in the vicinity of environmental surroundings inhabited by multicellular organisms ranging from achordates to chordates (including humans) (Kimbrell D A, Bender B. The evolution and genetics of innate immunity. Nat Rev Genet 2001, 2:256-267). For example, cells of immune system express various pattern recognition receptors (PRRs) that detect danger via recognizing specific pathogen-associated molecular patterns (PAMPs) and mount a specific immune response (Connolly D J., O'Neill L A. New developments in Toll-like receptor targeted therapeutics. Curr Opin Pharmacol 2012, 12:510-518). Toll-like receptors (TLRs) are one of these PRRs expressed by various immune cells. It has been estimated that most: mammalian species have between ten and 15 types of Tia. Thirteen TLRs (named simply TUR I to TLR13) have been identified in humans and mice together, and equivalent forms of many of these have been found in other mammalian species (Chuang T H, Ulevitch R J. Cloning and characterization of a sub-family of human toll-like receptors: hTLR7, hTLR8 and hTLR9. Eur Cytokine Netw 2000. 11:372-378, Du X, Poltorak A, Wei Y, Beutler B. Three novel mammalian toll-like receptors: gene structure, expression, and evolution. Eur Cytokine Netw 2000; 11:362-371; Tabeta K, Georgel P, Janssen E, Du X, Hoebe K, Crozat K, Mudd S, Shamel L., Sovath S, Goode J. Alexopoulou L, Favell R A, Beutler B. Toll-like receptors 9 and 3 as essential components of innate immune defense against mouse cytomegalovirus infection. Proc Nal Acad Sci U S A 2004; 101:3516-3521). Specifically, TLRs are single, membrane-spanning, noncatalytic receptors usually expressed on members of the innate or adaptive immune system [i.e. dendritic cells, macro-phages, granulocytes, T cells. B cells, natural killer (NK) cells and mast cells], as well as by endothelial and epithelial cells (Pichlmair A, Reis e Sousa C. Innate recognition of viruses, Immunity 2007, 27:370-383). TLRs have also been associated with the pathogenesis of several human cancers including B cell malignancies, colorectal cancer, hepatocellular carcinoma, basal cell carcinoma, bladder cancer, including several other cancers (Zou H, Wang W K, Liu Y L, Braddock M, Zheng M H, Huang D S. Toll-like receptors in hepatocellular carcinoma: potential novel targets for pharmacological intervention. Expert Opin Ther Targets 2016; 20: 1127-1135; Basith S, Manavalan B, Yoo T H, Kim S G, Choi S. Roles of toll-like receptors in cancer: a double-edged sword for defense and offense. Arch Pharm Res 2012; 35:1297-1316:, Basith S, Manavalan B, Yoo T H, Kim S G, Choi S. Roles of toll-like receptors in cancer, a double-edged sword for defense and offense. Arch Pharm Res 2012; 35:1297-1316; (Then R, Alvero A B, Silasi D A, Steffensen K D, Mor G. Cancers take their Toll-the function and regulation of Toll-like receptors in cancer cells. Oncogene 2008; 27.225-233:, Huang B, Zhao J, Unkeless J C, Feng Z H, Xiong H. TLR signaling by tumor and immune cells: a double-edged sword. Oncogene 2008; 27:218-224; Isaza-Correa J M, Lang Z, van den Berg A, Diepstra. A, Visser L. Toll-like receptors in the pathogenesis of human B cell malignancies. J Hematol Oncol 2014; 7:57; Li T T, Ogino S, Qian Z R. Toll-like receptor signaling in colorectal cancer: carcinogenesis to cancer therapy. World J Gastroenterol 2014; 20:17699-17708).

TLRs are widely expressed in both tumor cells and tumor-infiltrating immune cells and are involved in the regulation of tumor pathogenesis and antitumor immune responses (Vijay K. Toll-like receptors in immunity and inflammatory diseases: Past, present, and future. Int Immunopharmacol 2018; 59;391-412). Increasing evidence strongly indicates that TLR signaling directly cross talks with the molecular processes of cell metabolism in tumor cells and/or different subsets of immune cells (Huang L, Xu H, Peng G. TLR-mediated metabolic reprogramming in the tumor microenvironment: potential novel strategies for cancer immunotherapy. Cell Mol Immunol 2018). Cellular energy metabolism controls the fate and biological functions of both malignant tumor cells and tumor-infiltrating immune cells in the tumor microenvironment. The functional role of TLR signaling in reprogramming cell metabolism in the tumor microenvironment has been explored.

At molecular level, TLRs trigger activation of the nuclear factor kappa-light-chain-enhancer of activated B (NF-kB) pathway, which regulates the production of inflammatory cytokines such as interleukin (IL)-1, IL-6, IL-8, tumor necrosis factor (TNF)-a, IL-12, chemokines and induction of molecules such as CD80, CD86 and CD40 (Holldack J. Toll-like receptors as therapeutic targets for cancer, Drug Discov Today 2014, 19:379-382). In this way, TLRs are integrally involved in the processes of inflammation and immunity and indirectly in the control of apoptosis itself (Kawai T, Akira S. innate immune recognition of viral infection, Nat Immunol 2006, 7:131-137), Evidence implicates the involvement of the TLR family in a spectrum of systemic disorders following bacterial infections including sepsis, cardiac ischemia, periodontitis and cerebral palsy A sizeable body of research now exists demonstrating that the innate immune system has a significant role in protecting the body against progressive growth of primary non-viral cancers (Smyth M J, Dunn G P, Schreiber R D. Cancer immunosurveillance and immunoediting: the roles of immunity in suppressing tumor development and shaping tumor immunogenicity. Adv Immunol 2006; 90:1-50). Agonists of TLRs 3, 4, 7, 8 and 9 are considered important as potential immune therapeutics (Cheever M A. Twelve immunotherapy drugs that could cure cancers Immunol Rev 2008; 222:357-368) including adjuvants in vaccines (Wu T Y. Strategies for designing synthetic immune agonists. Immunology 2016; 148:315-325) and are included in the National Cancer Institute ranked list of therapeutic agents with the highest potential to treat cancer These include agonists utilizing live or killed bacteria, viral agents and synthetic small molecule compounds TLR activation is an effective means of achieving anti-tumor immune reactions via several related mechanisms. For a start, dendritic cells activated via TLRs drive increased phagocytosis, maturation with upregulation of major histocompatibility complex (MHC) and co-stimulatory molecules (CD80, CD86 and CD40), secretion of proinflammatory cytokines (especially and antigen presentation to lymphocytes resulting in the generation of effector T cells and antigen-specific B cells. Local TLR activation can also mobilize NK cell mediated cytotoxicity, upregulate MHC class 1. expression on tumor cells, directly induce apoptosis of tumor tissue and create an inflammatory environment conducive to activation of the full immune response (Sherman K, Liu Y J. Mouse and human dendritic cell subtypes; Nat Rev Immunol 2002; 2:151-161). Production of TLR agonist requires careful design to ensure efficacy. Through case studies with SAR analysis, TLR-agonist crystal structure evaluation, and molecular modeling, several important considerations were learnt when designing TLR agonists. TLR agonist discovery and chemical insights in effective TLR agonist conjugation will accelerate the ongoing developments at the forefront of vaccine and immunotherapy development.

Nevertheless, the therapeutics and methods currently available for the management of diseases or disorders associated with TLRs 7 and 8 remain inadequate. There is an urgent and ongoing need for novel and improved therapeutics to effectively treat such diseases and conditions.

SUMMARY OF THE INVENTION

The invention is based in part on the unexpected discovery of novel phosphorus imidazoquinoline amine derivatives, which are agonists of TLRs, in particular TLR7 and/or TLR8, pharmaceutical compositions thereof, and methods of treatment, reduction or prevention of certain diseases or conditions mediated by or associated with TLR7 and/or TLR8, e.g., graft rejection, autoimmunity, inflammation allergy, asthma, infection, sepsis, cancer and immunodeficiency, and related diseases and conditions.

In one aspect, the invention generally relates to a compound having the structural formula of (I):

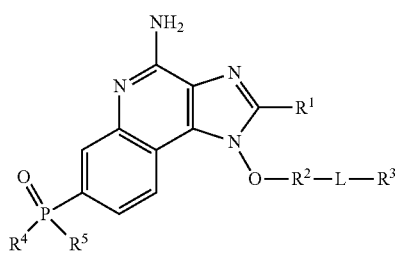

(I)

wherein,
$R^1$ is a $C_1$-$C_8$ alkyl group;
$R^2$ is $(CH_2)_m$, wherein m is an integer selected from 1 to 8;
L is a linking moiety;
$R^3$ is a H, or $C_1$-$C_{32}$ alkyl group; and
each of $R^4$ and $R^5$ is independently a $C_1$-$C_6$ aliphatic group; provided that $R^4$ and $R^5$, together with atoms to which they are bonded to, may optionally form a 5- to 7-membered aliphatic ring, or a pharmaceutically acceptable forum or an isotope derivative thereof.

In another aspect, the invention generally relates to a pharmaceutical composition comprising a compound disclosed herein.

In yet another aspect, the invention generally relates to a pharmaceutical composition comprising an amount of a compound having the structural formula of (I):

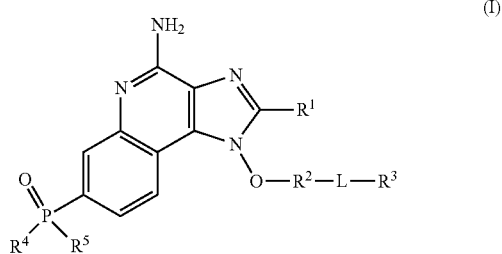

(I)

wherein,
$R^1$ is a $C_1$-$C_8$ alkyl group;
$R^2$ is $(CH_2)_m$, wherein in is an integer selected from 1 to 8;
L is a linking moiety;
$R^3$ is a H, or $C_1$-$C_{32}$ alkyl group; and
each of $R^4$ and $R^5$ is independently a $C_1$-$C_6$ aliphatic group; provided that $R^4$ and $R^5$, together with atoms to which they are bonded to, may optionally form a 5- to 7-membered aliphatic ring, or a pharmaceutically acceptable form or an isotope derivative thereof, effective to treat, prevent, or reduce one or more diseases or disorders, in a mammal, including a human, and a pharmaceutically acceptable excipient, carrier, or diluent.

In yet another aspect, the invention generally relates to a unit dosage form comprising a compound disclosed herein.

In yet another aspect, the invention generally relates to a unit dosage form comprising a pharmaceutical composition disclosed herein.

In yet another aspect, the invention generally relates to a method for treating, reducing, or preventing a disease or disorder, comprising administering to a subject in need thereof a pharmaceutical composition comprising a compound having the structural formula (I):

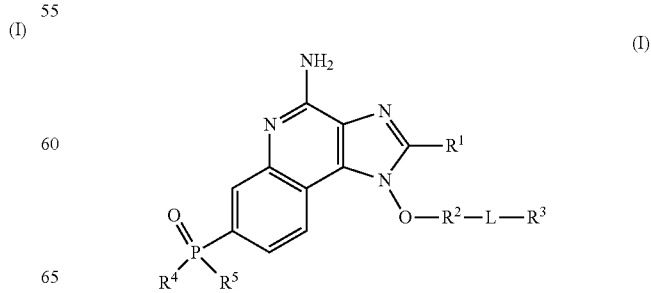

(I)

wherein, $R^1$ is a $C_1$-$C_8$ alkyl group;

$R^3$ is $(CH_2)_m$, wherein m is an integer selected from 1 to 8;

L is a linking moiety;

$R^3$ is a H, or $C_1$-$C_{32}$ alkyl group; and each of $R^4$ and $R^5$ is independently a $C_1$-$C_6$ aliphatic group; provided that $R^1$ and $R^5$, together with atoms to which they are bonded to, may optionally form a 5- to 7-membered aliphatic ring, or a pharmaceutically acceptable form or an isotope derivative thereof, effective to treat, reduce or prevent or one or more of autoimmune diseases, graft rejection, allergies, immunodeficiency, infection, sepsis, cancer, or a related disease or disorder thereof, in a mammal, including, a human, and a pharmaceutically acceptable excipient, carrier, or diluent.

In yet another aspect, the invention generally relates to a method for modulating immune response, comprising administering to a subject in need thereof a pharmaceutical composition comprising a compound disclosed herein.

In yet another aspect, the invention generally relates to a method for modulating TLR7- and/or TLR8-mediated signaling, comprising administering to a subject in need thereof a pharmaceutical composition comprising a compound disclosed herein.

In yet another aspect, the invention generally relates to a method for of treating, reducing, or preventing a condition or disorder treatable by modulation of TLR7- and/or TLR8-mediated cellular activities, comprising administering to a subject in need thereof a pharmaceutical composition comprising a compound disclosed herein.

In yet another aspect, the invention generally relates to a method for treating, reducing, or preventing a disease or disorder, comprising administering to a subject in need thereof a pharmaceutical composition comprising a compound disclosed herein, wherein the disease or disorder is autoimmune diseases, graft rejection, allergies, immunodeficiency, infection, sepsis, cancer, or a related disease or disorder.

In yet another aspect, the invention generally relates to use of a compound disclosed herein for treating, reducing or preventing a disease or disorder.

In yet another aspect, the invention generally relates to use of a compound disclosed herein and a pharmaceutically acceptable excipient, carrier, or diluent, in preparation of a medicament for treating, reducing or preventing a disease or disorder.

DEFINITIONS

Unless defined otherwise, all technical and scientific terms used herein have the same meaning as commonly understood by one of ordinary skill in the art to which this invention belongs. General principles of organic chemistry, as well as specific functional moieties and reactivity, are described in "Organic Chemistry", Thomas Sorrell, University Science Books, Sausalito: 1999, and "March's Advanced Organic Chemistry", $5^{th}$ Ed.: Smith, M. B. and March. J., John Wiley & Sons, New York: 2001, the entire contents of which are hereby incorporated by reference.

Certain compounds of the present invention may exist in particular geometric or stereoisomeric forms . . . The present invention contemplates all such compounds, including cis- and trans-isomers, R- and S-enantiomers, diastereomers, (D)-isomers, (L)-isomers, the racemic mixtures thereof and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers . . . Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic methods well known in the art, and subsequent recovery of the pure enantiomers.

Solvates and polymorphs of the compounds of the invention are also contemplated herein, Solvates of the compounds of the present invention include, for example, hydrates.

Definitions of specific functional groups and chemical terms are described in more detail below. When a range of values is listed, it is intended to encompass each value and sub-range within the range. For example, "$C_{6-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $c_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, the term "alkyl" refers to a straight, branched or cyclic hydrocarbon radical consisting solely of carbon and hydrogen atoms, containing no unsaturation, having from one to ten carbon atoms (e.g., $C_1$-$C_{10}$ alkyl). Whenever it appears herein, a numerical range such as "1 to 10" refers to each integer in the given range; e.g., "1 to 10 carbon atoms" means that the alkyl group can consist of 1 carbon atom, 2 carbon atoms, 3 carbon atoms, up to and including 10 carbon atoms, although the present definition also covers the occurrence of the term "alkyl" where no numerical range is designated. In some embodiments, "alkyl" can be a $C_{1-6}$ alkyl group. In some embodiments, alkyl groups have 1 to 10, 1 to 8, 1 to 6, to 1 to 3 carbon atoms.

Representative saturated straight chain alkyls include, but are not limited to, -methyl, -ethyl, -n-propyl, -n-pentyl, and -n-hexyl; while saturated branched alkyls include, but are not limited to, -isopropyl, -sec-butyl, -isobutyl, -teat-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, and the like, The alkyl is attached to the parent molecule by a single bond.

Unless stated otherwise in the specification, an alkyl group is optionally substituted by one or more of substituents which independently include: acyl, alkenyl, alkynyl, alkoxy, alkylaryl, cycloalkyl, aralkyl, aryloxy, ammo, amido, amidino, imino, azide, carbonate, carbamate, carbonyl, heteroalkyl, heteroaryl, heteroarylalkyl, heterocycloalkyl, hydroxy, cyano, halo (F, Cl, Br, O, haloalkoxy, haloalkyl, ester, ether, mercapto, thio, alkylthio, arylthio, thiocarbony nitro, oxo, phosphate, phosphonate, phosphinate, silyl, sulfonamidyl, sulfoxyl, sulfonate, urea. —Si(R$^a$)$_3$, —OR$^a$, —SR$^a$, —OC(O)—R$^a$, —N(R$^a$)$_2$, —C(O)R$_a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$N(R$^a$)$_2$ (where t is 1 or 2), —P(=O)(R$^a$)(R$^a$), or —O—P(=O)(OR$^a$)$_2$ where each R$^a$ is independently hydrogen, alkyl, haloalkyl, carbocyclyl, carbocydylalkyl, aryl, aralkyl, heterocycloalkyl, heterocycloalkyl alkyl, heteroaryl or heteroarylalkyl, and each of these moieties can be optionally substituted as defined herein. In a non-limiting embodiment, a substituted alkyl can be selected from fluoromethyl, difluoromethyl, trifluoromethyl, 2-fluoroethyl, 3-fluoropropyl-hydroxymethyl, 2-hydroxyethyl, 3-hydroxypropyl, benzyl, and phenethyl.

As used herein, the terms "aliphatic" or "aliphatic group" means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, hut Which is not aromatic, that has a single point of attachment to the rest of the molecule . . . Unless otherwise specified, aliphatic groups contain 1-6 aliphatic carbon atoms . . . In some embodiments, aliphatic groups contain 1-5 aliphatic carbon atoms . . . In other embodiments, aliphatic groups contain 1-4 aliphatic carbon atoms . . . In still other embodiments, aliphatic groups contain 1-3 aliphatic carbon atoms, and in yet other embodiments, aliphatic groups contain 1-2 aliphatic carbon atoms. In some embodiments, "cycloaliphatic" refers to a monocylic C$_3$-C$_6$ hydrocarbon that is completely saturated or that contains one or more units of unsaturation, but which is not aromatic, that has a single point of attachment to the rest of the molecule. Exemplary aliphatic groups are linear or branched, substituted or unsubstituted C$_1$-C$_8$ alkyl, C$_2$-C$_8$ alkenyl, C$_2$-C$_8$ alkynyl groups and hybrids thereof such as (cycloalkyl)alkyl, (cycloalkenyl)alkyl or (cycloalkyl)alkenyl.

As used herein, the term "heteroatom" means one or more of oxygen, sulfur, nitrogen, or phosphorus (including, any oxidized form of nitrogen, sulfur, or phosphorus; the quaternized form of any basic. nitrogen or, a substitutable nitrogen of a heterocyclic ring, for example N (as in 3,4-dihydro-2H-pyrrolyl)-NH (as in pyrrolidinyl) or NR$^+$ (as in N-substituted pyrrolidinyl)).

The term "unsaturated", as used herein, means that a moiety has one or more units of unsaturation.

As used herein, the term "alkylene" refers to a bivalent alkyl group . . . An "alkylene chain" is a poly methylene group, i.e., —(CH$_2$)$_n$—, wherein n is a positive integer, preferably from 1 to 6, fro 1 to 4, from 1 to 3, from 1 to 2, or from 2 to 3. A substituted alkylene chain is a polymethylene group in which one or more methylene hydrogen atoms are replaced with substituent. Suitable substituents include those described below for a substituted aliphatic group.

As used herein, the term "halogen" refers to fluorine (F), chlorine (Cl), bromine (Br), or iodine (I). As used herein, the term "halide" or "halo", means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine, such as, but not limited to, trifluoromethyl, difluoromethyl, 2,2,2-trifluoroethyl, 1-fluoromethyl-2-fluoroethyl, and the like. Each of the alkyl, alkenyl, alkynyl and alkoxy groups are as defined herein and can be optionally further substituted as defined herein.

As used herein, the term "alkoxy" refers to the group —O-alkyl, including from 1 to 10 carbon atoms (C$_{1-10}$) of a straight, branched, saturated cyclic configuration and combinations thereof, attached to the parent molecular structure through an oxygen. Examples include methoxy, ethoxy, propoxy, isoptopoxy, butoxy t-butoxy, pentoxy, cyclopropyloxy, cyclohexyloxy and the like. "Lower alkoxy" refers to aikoxy groups containing one to six carbons. In sonic embodiments, C$_{1-3}$ alkoxy is an alkoxy group that encompasses both straight and branched chain alkyls of from 1 to 3 carbon atoms. Unless stated otherwise in the specification, an alkoxy group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$, —N(R$^a$)$_2$, —C(O)R$_a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$N(R$^a$)$_2$ (where t is 1 or 2), —P(=O)(R$^a$)(R$^a$), or —O—P(=O)(OR$^a$)$_2$ where each R$^a$ is independently hydrogen, alkyl, haloalkyl, carbocyclyl, carbocyclylalkyl, aryl, aralkyl, heterocycloalkyl, heterocycloalkyalkyl heteroaryl or heteroarylalkyl, and each of these moieties can be optionally substituted as defined herein.

As used herein, the terms "aromatic" or "aryl" refer to a radical with 6 to 14 ring atom's (e.g., C$_{6-14}$ aromatic or C$_{6-14}$ aryl) that has at least one ring having a conjugated pi electron system which is carbocyclic (e.g., phenyl, fluorenyl, and naphthyl). In some embodiments, the aryl is a C$_{6-10}$ aryl group. For example, bivalent radicals formed from substituted benzene derivatives and having the free valences at ring atoms are named as substituted phenylene radicals. In other embodiments, bivalent radicals derived from univalent polycyclic hydrocarbon radicals those names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 14 aryl" refers to each integer in the given range, e.g., "6 to 14 ring atoms" means that the aryl group can consist of 6 ring atoms, 7 ring atoms, etc., up to and including 14 ring atoms. The term includes monocyclic or fused-ring polycyclic (i.e., rings which share adjacent pairs of ring atoms) groups. Polycyclic aryl groups include bicycles, tricycles, tetracycles, and the like. In a multi-ring group, only one ring is required to be aromatic, so groups such as indanyl are encompassed by the aryl definition. Non-limiting examples of aryl groups include phenyl, phenalenyl, naphthatenyl, tetrahydronaphthyl, phenanthrenyl, anthracenyl, fluorenyl, indolyl, indanyl, and the like. Unless stated otherwise in the specification, an aryl moiety can be optionally substituted by one or more substituents which independently include: acyl, alkyl, alkenyl, alkynyl, alkoxy, alkylaryl, cycloalkyl, aralkyl, aryl, aryloxy, amino, amido, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R_a$, —C(O)O$R^a$, —OC(O)N($R^a$)$_2$, —C(O)N($R^a$)$_2$, —N($R^a$)c(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)(O$R^a$)$_2$ where $R^a$ is independently hydrogen, alkyl, haloalkyl, carbocyclyl, carbocyclylalkyl, aryl, aralkyl, heterocycloalkl, heterocycloalkylalkyl, heteroaryl or heteroarylalkyl, and each of these moieties can be optionally substituted as defined herein.

As used herein, the terms "cycloalkyl" and "carbocyclyl" each refers to a monocyclic or polycyclic radical that contains only carbon and hydrogen, and can be saturated or partially unsaturated. Partially unsaturated cycloalkyl groups can be termed "cycloalkenyl" if the carbocycle contains at least one double bond, or "cycloalkynyl" if the carbocycle contains at least one triple bond. Cycloalkyl groups include groups having from 3 to 13 ring atoms (i e., $C_{3-13}$ cycloalkyl). Whenever it appears herein, a numerical range such as "3 to 10" refers to each integer in the given range, e.g., "3 to 13 carbon atoms" means that the cycloalkyl group can consist of 3 carbon atoms, 4 carbon atoms, 5 carbon atoms, etc., up to and including 13 carbon atoms. The term "cycloalkyl" also includes bridged and Spiro-fused cyclic structures containing no heteroatoms. The term also includes monocyclic or fused-ring polycyclic (i.e., rings which share adjacent pairs of ring atoms) groups. Polycyclic aryl groups include bicycles, tricycles, tetracycles, and the like. In some embodiments, "cycloalkyl" can be a $C_{3-8}$ cycloalkyl radical. In some embodiments, "cycloalkyl" can be a cycloalkyl radical. Illustrative examples of cycloalkyl groups include, but are not limited to the following moieties: $C_{3-6}$ carbocyclyl groups include, without limitation, cyclopropyl cyclobutyl ($C_4$), cyclopentyl ($C_5$), cyclopentenyl ($C_5$), cyclohexyl ($C_6$), cyclohexenyl ($C_6$), cyclohexadienyl ($C_6$) and the like, Examples of $C_{3-7}$ carbocyclyl groups include norbornyl ($C_7$) . . . Examples of carbocyclyl groups include the aforementioned $C_{3-7}$ carbocyclyl groups as well as cycloheptyl ($C_7$), cycloheptadienyl ($C_7$), cycloheptatrienyl ($C_7$), cyclooctyl ($C_8$), bicyclo[2.2.1]heptanyl, bicyclo[2.2.2]octanyl, and the like. Examples of $C_{3-13}$; carbocyclyl groups include the aforementioned $C_{3-8}$ carbocyclyl groups as well as octahydro-1H indenyl, decahydronaphthalenyl, spiro[4.5]decanyl and the like. Unless stated otherwise in the specification, a cycloalkyl group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl sulfonyl, sulfonamidyl, sulfoxyl, sulfonate- urea, —Si($R^a$)$_3$, —O$R^a$, —S$R^a$, —OC(O)—$R^a$, —N($R^a$)$_2$, —(O)$R_a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)(O$R^a$)$_2$ where each $R^a$ is independently hydrogen, alkyl, haloalkyl, carbocyclyl, carbocyclyalkyl, aryl, aralkyl, heterocycloalkyl, heterocycloalkylalkyl. heteroaryl or heteroarylalkyl, and each of these moieties can be optionally substituted as defined herein. The terms "cycloalkenyl" and "cycloalkynyl" mirror the above description of "cycloalkyl" wherein the prefix "alk" is replaced with "alken" or "alkyn" respectively, and the parent "alkenyl" or "alkynyl" terms are as described herein . . . For example, a cycloalkenyl group can have 3 to 13 ring atoms, such as 5 to 8 ring atoms . . . In some embodiments, a cycloalkynyl group can have 5 to 13 ring atoms.

As used herein, the term "heteroalkyl" refers to an alkyl radical, which have one or more skeletal chain atoms being an atom other than carbon, e.g., oxygen, nitrogen, sulfur, phosphorus or combinations thereof. A numerical range can be given, e.g., $C_{1-1}$ heteroalkyl, which refers to the chain length in total, which in this example is 4 atoms long. For example, a —CH$_2$OCH$_2$CH$_3$ radical is referred to as a "$C_4$" heteroalkyl, which includes the heteroatom center in the atom chain length description. connection to the parent molecular structure can be through either a heteroatom or a carbon in the heteroalkyl chain. For example, an N-containing heteroalkyl moiety refers to a group in which at least one of the skeletal atoms is a nitrogen atom. One or more heteroatom(s) in the heteroalkyl radical can be optionally oxidized. One or more nitrogen atoms, if present, can also be optionally quaternized. For example, heteroalkyl also includes skeletal chains substituted with one or more nitrogen oxide (—O—) substituents. Exemplary heteroalkyl groups include, without limitation, ethers such as methoxyethanyl (—CH$_2$CH$_2$OCH$_3$), ethoxymethanyl (—CH$_2$OCH$_2$CH$_3$), (methoxymethoxy)ethanyl (—CH$_2$C$_2$OCH$_2$OCH$_3$), (methoxymethoxy) methanyl(—CH$_2$OCH$_2$OCH$_3$) and (methoxyethoxy)methanyl (—CH$_2$OCH$_2$CH$_2$OCH$_3$) and the like; .amines such as (—CH$_2$CH$_2$NHCH$_3$, —CH$_2$CH$_2$N(CH$_3$)$_2$, —CH$_2$NHCH$_2$CH$_3$, —CH$_2$N(CH$_2$CH$_3$)(CH$_3$)) and the like.

As used herein, the term "heteroaryl" or "heteroaromatic" refers to a refers to a radical of a 5-18 membered monocyclic or polycyclic (e.g., bicyclic, tricyclic, tetracyclic and the like) aromatic ring system (e.g., having 6, 10 or 14 π electrons shared in a cyclic array) having ring carbon atoms and 1-6 ring heteroatoms provided in the aromatic ring system, wherein each heteroatom is independently selected from nitrogen, oxygen, phosphorous and sulfur. Heteroaryl polycyclic ring systems can include one or more heteroatoms in one or both rings. Whenever it appears herein, a numerical range such as "5 to 18" refers to each integer in the given range; e.g., "5 to 18 ring atoms" means that the heteroaryl group can consist of 5 ring atoms, 6 ring atoms, etc., up to and including 18 ring atoms, In some instances, a heteroaryl can have 5 to 14 ring atoms. In some embodiments, the heteroaryl has, for example, bivalent radicals derived from univalent heteroaryl radicals whose names end in "-yl" by removal of one hydrogen atom from the atom with the free valence are named by adding "-ene" to the name of the corresponding univalent radical, e.g, a pyridyl group with two points of attachment is a pyridylene.

For example, an N-containing, "heteroaromatic" "heteroaryl" moiety refers to an aromatic group in which at least one of the skeletal atoms of the ring is a nitrogen atom. One or more heteroatom(s) in the heteroaryl radical can be optionally oxidized. One or more nitrogen atoms, if present, can also be optionally quaternized. Heteroaryl also includes ring systems substituted with one or more nitrogen oxide (—O—) substituents, such as pyridinyl N-oxides. The heteroaryl is attached to the parent molecular structure through any atom of the ring(s).

"Heteroaryl" also includes ring systems wherein the heteroaryl ring, as defined above, is fused with one or more aryl groups wherein the point of attachment to the parent molecular structure is either on the aryl or on the heteroaryl ring, or wherein the heteroaryl ring, as defined above, is fused with one or more cycloalkyl or heterocycyl groups wherein the point of attachment to the parent molecular structure is on the heteroaryl ring. For polycyclic heteroaryl groups wherein one ring does not contain a heteroatom (e.g., indolyl, quinolinyl, carbazolyl and the like), the point of attachment to the parent molecular structure can be on either ring, i.e., either the ring bearing a heteroatom (e.g 2-indolyl) or the ring that does not contain a heteroatom (e.g., 5-indolyl). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, phosphorous, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, phosphorous, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, phosphorous, and sulfur ("5-6 membered heteroaryl"). In some embodiments, the 5-6 membered heteroaryl has 1-3 ring heteroatoms selected from nitrogen, oxygen, phosphorous, and sulfur. In some embodiments, the 5-6 membered heteroaryl has 1-2 ring heteroatoms selected from nitrogen, oxygen, phosphorous, and sulfur. In some embodiments, the 5-6 membered heteroaryl has 1 ring heteroatom selected from nitrogen, oxygen, phosphorous, and sulfur.

Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzopyranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno [2,3-d]pyrimidinyl, 5,6-dihydrobenzo[h]quinazolinyl, 5,6-dihydrobenzo[h]cinnolinyl, 6,7-dihydro-5H benzo[6,7]cyclohepta[1,2-c]pyridazinyl, dibenzofuranyl, dibenzothiophenyl, furanyl, furazanyl, furanonyl, furo [3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10- hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phetlyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo [4,5]thieno [2,3-d]pyrimidinyl, 6,7,8,9-tetrahydro-5H-cyclohepta[4,5]thieno [2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e., thienyl). Unless stated otherwise in the specification, a heteroaryl moiety can be optionally substituted by one or more substituents which independently include acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$, —N(R$^a$)$_2$, —C(O)R$_a$, —C(O)OR$^a$, —OC(O)N(R$^a$)$_2$, —C(O)N(R$^a$)$_2$, —N(R$^a$)C(O)OR$^a$, —N(R$^a$)c(O)R$^a$, —N(R$^a$)C(O)N(R$^a$)$_2$, N(R$^a$)C(N-R$^a$)N(R$^a$)$_2$, —N(R$^a$)S(O)$_t$N(R$^a$)$_2$ (where t is 1 or 2), —P(=O)(R$^a$)(R$^a$), or —O—P(=O)(OR$^a$)$_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

As used herein, the terms "TLR7 and/or TLR8 ligand," "ligand for TLR7 and/or TLR8," and "TLR7 and/or signaling agonist" refer to a molecule, other than a compound disclosed herein, that interacts directly or indirectly with TLR7 and/or TLR8 through a TLR7 and/or TLR8 domain other than a TLR8 domain, and induces TLR7- and/or TLR8-mediated signaling. In certain embodiments, a TLR7 and/or TLR8 ligand is a natural ligand, i.e., a TLR7 and/or TLR8 ligand that is found in nature. In certain embodiments, a TLR7 and/or TLR8 ligand refers to a molecule other than a natural ligand of TLR7 and/or TLR8, e.g., a molecule prepared by human activity.

As used herein, the term "modulator" is defined as a compound that binds to and for activates or inhibits the target with measurable affinity, or directly or indirectly affecting the normal regulation of the receptor activity. In certain embodiments, a modulator has an EC$_{50}$ and/or binding constant of less about 50 μM, less than about 1 μM, less than about 500 nM, less than about 100 nM, or less than about 10 nM.

As used herein, the term "agonist" refers to a compound that, in combination with a receptor (e.g., a TLR), can produce a cellular response. An agonist may be a ligand that directly binds to the receptor. Alternatively, an agonist may combine with a receptor indirectly by, for example, (a) forming a complex with another molecule that directly binds to the receptor, or (b) otherwise resulting in the modification of another compound so that the other compound directly binds to the receptor. An agonist may be referred to as an agonist of a particular TLR (e.g., a TLR7 and/or TLR8 agonist).

As used herein, the term "antagonist" refers to a compound that competes with an agonist or inverse agonist for binding to a receptor, thereby blocking the action of an agonist or inverse agonist on the receptor However, an antagonist has no effect on constitutive receptor activity. More specifically, an antagonist is a compound that inhibits the activity of TLR7 or TLR8 at the TLR7 or TL8S receptor, respectively.

As used herein, the term "inhibit" refers to any measurable reduction of biological activity. Thus, as used herein, "inhibit" or "inhibition" may be referred to as a percentage of a normal level of activity.

As used herein, the term "effective amount" of an active agent refers to an amount sufficient to elicit the desired biological response . . . As will be appreciated by those of ordinary skill in this art, the effective amount of a compound of the invention may vary depending on such factors as the desired biological endpoint, the pharmacokinetics of the compound, the disease being treated, the mode of administration, and the patient.

As used herein, the terms "treatment" or "treating" a disease or disorder refers to a method of reducing, delaying or ameliorating such a condition before or after it has occurred. Treatment may be directed at one or more effects or symptoms of a disease and or the underlying pathology. The treatment can be any reduction and can be, but is not limited to, the complete ablation of the disease or the symptoms of the disease. As compared with an equivalent untreated control, such reduction or degree of prevention is at least 5%, 10%, 20%. 40%, 50%, 60%, 80%, 90%, 95%. ot 100% as measured by any standard technique.

As used herein, the terms "prevent", "preventing", or "prevention" refer to a method for precluding, delaying, averting, or stopping the onset, incidence, severity, or recurrence of a disease or condition. For example, a method is considered to be a prevention if there is a reduction or delay in onset, incidence, severity, or recurrence of a disease or condition or one or more symptoms thereof in a subject susceptible to the disease or condition as compared to a subject not receiving the method. The disclosed method is also considered to be a prevention if there is a reduction or delay in onset, incidence, severity, or recurrence of osteoporosis or one or more symptoms of a disease or condition in a subject susceptible to the disease or condition after receiving the method as compared to the subject's progression prior to receiving treatment. Thus, the reduction or delay in onset, incidence, severity, or recurrence of osteoporosis can be about a 5, 10, 20, 30, 40, 50, 60, 70, 80, 90, 100%, or any amount of reduction in between.

As used herein, a "pharmaceutically acceptable form" of a disclosed compound includes, but is not limited to, pharmaceutically acceptable salts, esters, hydrates, solvates, polymorphs, isomers, prodrugs, and isotopically labeled derivatives thereof. In one embodiment, a "pharmaceutically acceptable form" includes, but is not limited to, pharmaceutically acceptable salts, esters, prodrugs and isotopically labeled derivatives thereof in some embodiments, a "pharmaceutically acceptable form" includes, but is not limited to, pharmaceutically acceptable isomers and stereoisomers, prodrugs and isotopically labeled derivatives thereof.

In certain embodiments, the pharmaceutically acceptable form is a pharmaceutically acceptable salt. As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit risk ratio. Pharmaceutically acceptable salts are well known in the art. For example, Berge et al. describes pharmaceutically acceptable salts in detail in *J. Pharmaceutical Sciences* (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or maionic acid or by using, other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lautyl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, organic acids from which salts can be derived include, for example, acetic acid, propionic acid, glycolic acid, pyruvic acid, oxalic acid, lactic acid, trifluoracetic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The salts can be prepared in situ during the isolation and purification of the disclosed compounds, or separately, such as by reacting the free base or free acid of a parent compound with a suitable base or acid, respectively. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, iron, zinc, copper, manganese, aluminurn, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl suifonate and aryl sulfonate. Organic bases from which salts can be derived include, for example, primary, secondary, and tertiary amines, substituted amines, including naturally occurring substituted amines, cyclic amines, basic ion exchange resins, and the like, such as isopropylamine, trimethylamine-diethylamine, triethylamine, tripropylamine, and ethanolamine. In some embodiments, the pharmaceutically acceptable base addition salt can be chosen from ammonium, potassium, sodium, calcium, and magnesium salts.

In certain embodiments, the pharmaceutically acceptable form is a "solvate" (e.g., a hydrate). As used herein, the term "solvate" refers to compounds that further include a stoichiometric or non-stoichiometric amount of solvent bound by non-covalent intermolecular forces. The solvate can be of a disclosed compound or a pharmaceutically acceptable salt thereof. Where the solvent is water, the solvate is a "hydrate". Pharmaceutically acceptable solvates and hydrates are complexes that, for example, can include 1 to about 100, or 1 to about 10, or 1 to about 2, about 3 or about 4, solvent or water molecules. it will be understood that the term "compound" as used herein encompasses the compound and solvates of the compound, as well as mixtures thereof.

In certain embodiments, the pharmaceutically acceptable form is a prodrug. As used herein, the term "prodrug" (or "pro-drug") refers to compounds that are transformed in vivo to yield a disclosed compound or a pharmaceutically acceptable form of the compound. A prodrug can be inactive when administered to a subject, but is converted in vivo to an active compound, for example, by hydrolysis (e.g., hydrolysis in blood). In certain cases, a prodrug has improved physical and/or delivery properties over the parent compound. Prodrugs can increase the bioavailability of the compound when administered to a subject (e.g., by permitting enhanced absorption into the blood following oral administration) or which enhance delivery to a biological compartment of interest (e.g., the brain or lymphatic system) relative to the parent compound. Exemplary prodrugs include derivatives of a disclosed compound with enhanced aqueous solubility or active transport through the gut membrane, relative to the parent compound.

The prodrug compound often offers advantages of solubility, tissue compatibility or delayed release in a mammalian organism (see, Bundgard, H., Design of Prodrugs (1985), pp. 7-9, 21-24 (Elsevier, Amsterdam) A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B, Roche, American Pharmaceutical Association and Pergamon Press, 1987, both of which are incorporated in full by reference herein Exemplary advantages of a prodrug can include, but are not limited to, its physical properties, such as enhanced water solubility for parenteral administration at physiological pH compared to the parent compound, or it can enhance. absorption from the digestive tract, or it can enhance drug stability for long-term storage.

Prodrugs commonly known in the art include well-known acid derivatives, such as, for example, esters prepared by reaction of the parent acids with a suitable alcohol, amides prepared by reaction of the parent acid compound with an amine, basic groups reacted to form an acylated base derivative, etc.. Of course, other prodrug derivatives may be combined with other features disclosed herein to enhance such, those of skill in the art will appreciate that certain of the presently disclosed compounds having free amino, amido, hydroxy or carboxylic groups can be converted into prodrugs. Prodrugs include compounds having art amino acid residue, or a poly peptide chain of two or more (e.g., two, three or four) amino acid residues which are covalently joined through peptide bonds to free amino, hydroxy or carboxylic acid groups of the presently disclosed compounds. The amino acid residues include the 20 naturally occurring amino acids commonly designated by three letter symbols and also include 4-hydroxyproline, by droxylysine, demosine, isodemosine, 3-methylhistidine, norvalin, beta-alanine, gamma-aminobutyric acid, citrulline homocysteine, homoserine, ornithine and methionine sulfone. Prodrugs also include compounds having a carbonate, carbamate, amide or alkyl ester moiety covalently bonded to any of the above substituents disclosed herein.

As used herein, the term "pharmaceutically acceptable" excipient, carrier, or diluent refers to a pharmaceutically acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient . . . Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil, glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water, isotonic saline; Ringer's solution; ethyl alcohol; phosphate buffer solutions; and other non-toxic compatible substances employed in pharmaceutical formulations . . . Wetting intents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

As used herein, the terms "isolated" or "purified" refer to a material that is substantially or essentially free front components that normally accompany it in its native state. Purity and homogeneity are typically determined using analytical chemistry techniques such as polyacrylamide gel electrophoresis or high-performance liquid chromatography.

As used herein, the term "subject" refers to any animal (e.g., a mammal), including, but riot limited to humans, non-human primates, rodents, and the like, which is to be the recipient of a particular treatment. Typically, the terms "subject" and "patient" are used interchangeably herein in reference to a human subject.

As used herein, the term "low dosage" refers to at least 5% less (e.g., at least 10%, 20%, 50%, 80%, 90%, or even 95%) than the lowest standard recommended dosage of a particular compound formulated for a given route of administration for treatment of any human disease or condition. For example, a low dosage of an agent that is formulated for administration by inhalation will differ from a low dosage of the same agent formulated for oral administration.

As used herein, the term "high dosage" is meant at least 5% (e.g., at least 10%, 20%, 50%, 100%, 200%, or even 300%) more than the highest standard recommended dosage of a particular compound for treatment of any human disease or condition.

Isotopically-labeled compounds are also within the scope of the present disclosure. As used herein, an "isotopically-labeled compound" or "isotope derivative" refers to a presently disclosed compound including pharmaceutical salts and prodrugs thereof, each as described herein, in which one or more atoms are replaced by an atom having an atomic mass or mass number different from the atomic mass or mass number usually found in nature. Examples of isotopes that can be incorporated into compounds presently disclosed include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

By isotopically-labeling the presently disclosed compounds, the compounds may be useful in drug and/or substrate tissue distribution assays. Tritiated ($^3$H) and carbon-14 ($^{14}$C) labeled compounds are particularly preferred for their ease of preparation and detectability. Further, substitution with heavier isotopes such as deuterium ($^2$H) can afford certain therapeutic advantages resulting from greater metabolic stability, for example increased in vivo half-life or reduced dosage requirements and, hence, may be preferred in some circumstances. Isotopically labeled compounds presently disclosed, including pharmaceutical salts, esters, and prodrugs thereof, can be prepared by any means known in the art. Benefits may also be obtained from replacement of normally abundant $^{12}$C with $^{13}$C. (See, WO 2007/005643, WO 2007/005644, WO 2007/016361, and WO 2007/016431)

For example, deuterium ($^2$H) can be incorporated into a compound disclosed herein for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D=2-7$ are typical. If this rate difference is successfully applied to a compound disclosed herein that is susceptible to oxidation, the profile of this compound in vivo can be drastically modified and result in improved pharmacokinetic properties.

When discovering and developing therapeutic agents, the person skilled in the art is able to optimize pharmacokinetic parameters while retaining desirable in vitro properties. It is reasonable to assume that many compounds with poor pharmacokinetic profiles are susceptible to oxidative metabolism, in vitro liver microsomal assays currently available provide valuable information on the course of oxidative metabolism of this type, which in turn permits the rational design of deuterated compounds of those disclosed herein with improved stability through resistance to such oxidative metabolism. Significant improvements in the pharmacokinetic profiles of compounds disclosed herein are thereby obtained, and can be expressed quantitatively in terms of increases in the in vivo half-life (t/2), concen-tra-tion at maximum therapeutic effect ($C_{max}$), area under the dose response curve (AUC), and F: and in terms of reduced clearance, dose and materials costs.

The following is intended to illustrate the above: a compound which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favorable and accurate determination of the extent of the extent to which the improvement in resistance to oxidative metabolism has improved. In this way, it is determined that the half-life of the parent compound can be extended by up to 100% as the result of deuterium-hydrogen exchange of this type.

Deuterium-hydrogen exchange in a compound disclosed herein can also be used to achieve a favorable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

Compounds of the present invention are, subsequent to their preparation, preferably isolated and purified to obtain a composition containing an amount by weight equal to or greater than 95% ("substantially pure"), which is then, used or formulated as described herein . . . . In certain embodiments, the compounds of the present invention are more than 99% pure.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

DETAILED DESCRIPTION OF THE INVENTION

The invention provides novel phosphorus imidazoquinoline amine derivatives, which are agonists of TLRs, in particular TLR7 and/or TLR8, pharmaceutical compositions thereof, and methods of treatment, reduction or prevention of certain diseases or conditions mediated by or associated with TLR7 and/or TLR8, e.g., graft rejection, autoimmunity, inflammation allergy, asthma, infection, sepsis, cancer and immunodeficiency, or related diseases and conditions.

In one aspect, the invention generally relates to a compound having the structural formula (I)

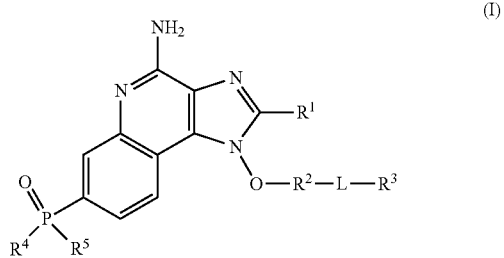

wherein, $R^1$ is a $C_1$-$C_8$ alkyl group;

$R^2$ is $(CH_2)_m$, wherein m is an integer selected from 1 to 8;

L is a linking moiety;

$R^3$ is a H, or $C_1$-$C_{23}$ alkyl group; and each of $R^4$ and $R^5$ is independently a $C_1$-$C_6$ aliphatic group, provided that $R^4$ and $R^5$, together with atoms to which they are bonded to, may optionally form a 5- to 7-membered aliphatic or a pharmaceutically acceptable form or an isotope derivative thereof.

In certain embodiments, each of $R^4$ and $R^5$ is independently a $C_1$-$C_6$ alkyl group.

In certain embodiments, each of $R_4$ and $R^5$ is independently selected from $CH_3$, $CH_2CH_3$ and $CH_2(CH_3)CH_3$.

In certain embodiments, $R^4$ and $R^5$ together with atoms to which they bonded form an aliphatic ring selected from:

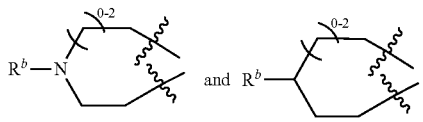

wherein $R^b$ is H, a $C_1$-$C_6$ alkyl or cycloalkyl group.

In certain embodiments, is $R^b$ is H. In certain embodiments, $R^b$ is a $C_1$-$C_3$ group (e.g., methyl, ethyl, cyclopropyl). In certain embodiments, $R^b$ is a 5- to 7- (e.g., 5-, 6-, 7-) membered cycloaliphatic (e.g., a heterocycloalkyl) group.

In certain embodiments, $R^3$ is a $C_3$-$C_6$ (e.g., $C_3$, $C_4$, $C_5$, $C_6$) alkyl group, m is an integer selected from 3 to 8 (e.g. 3, 4, 5, 6, 7, 8), and $R^3$ is a H, or a $C_{12}$-$C_{32}$ (e.g., $C_1$-$C_{16}$, $C_{16}$-$C_{32}$, $C_{16}$-$C_{24}$) alkyl group.

In certain embodiments, $R^1$ is a $C_4$ alkyl group, having the structural formula:

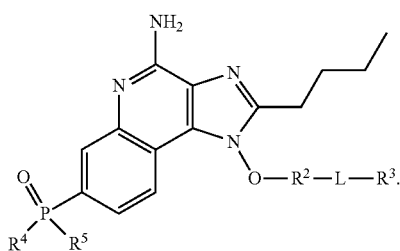

In certain embodiments, $R^1$ is a $C_4$ alkyl group and m is 4, having the structural formula:

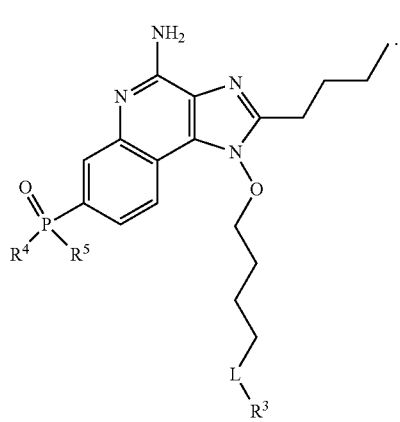

In certain embodiments, $R^1$ is a $C_4$ alkyl group and m is 4, each of $R^4$ and $R^5$ is methyl, having the structural formula:

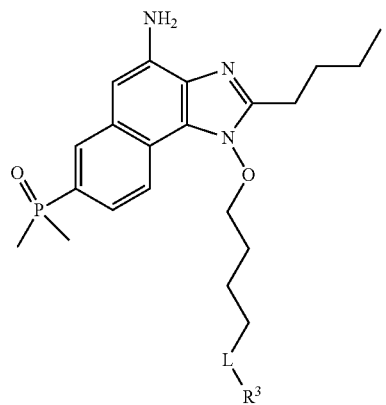

In certain embodiments, $R^2$ is a $C_{14}$-$C_{20}$ (e.g., $C_{14}$-$C_{16}$, $C_{16}$, $C_{18}$, $C_{18}$-$C_{20}$) alkyl group.

In certain embodiments, L comprises an amino group.

In certain embodiments, L is an acyclic group.

In certain embodiments, L comprises a 3- to 7- (e.g., 3- 4-, 5-, 6-, 7-) membered ring.

In certain embodiments, L is selected from.

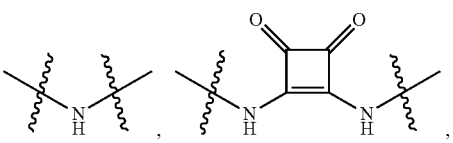

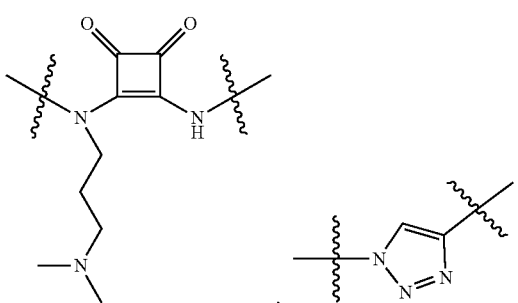

It is noted that the exemplary linkers (L) may be connected to the rest of the compound such that L is boned to $R^2$ on the left and to $R^3$ on the right, or may be connected to the rest of the compound such that L is bonded to $R^2$ on the right and to $R^3$ on the left.

Exemplary compounds of the invention include, but are not limited to, those listed in Table 1, or a pharmaceutically acceptable form or an isotope derivative thereof.

TABLE 1
Exemplary Compounds
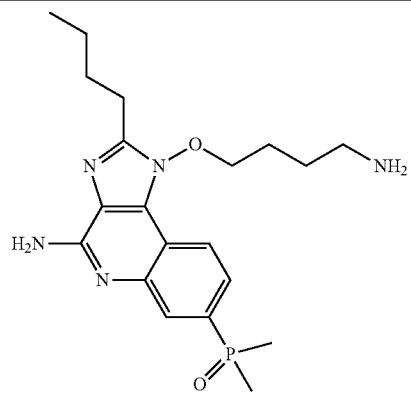
1
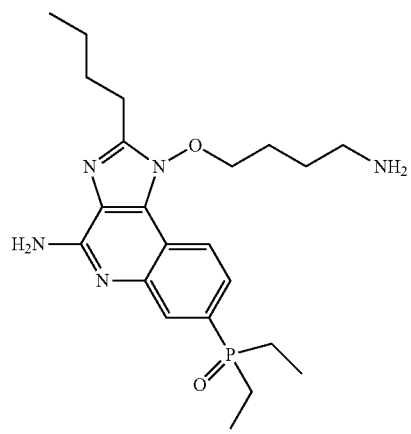 [SMILES: CCCCc1nc2c(N)nc3cc(P(=O)(CC)CC)ccc3c2n1OCCCCN]
2
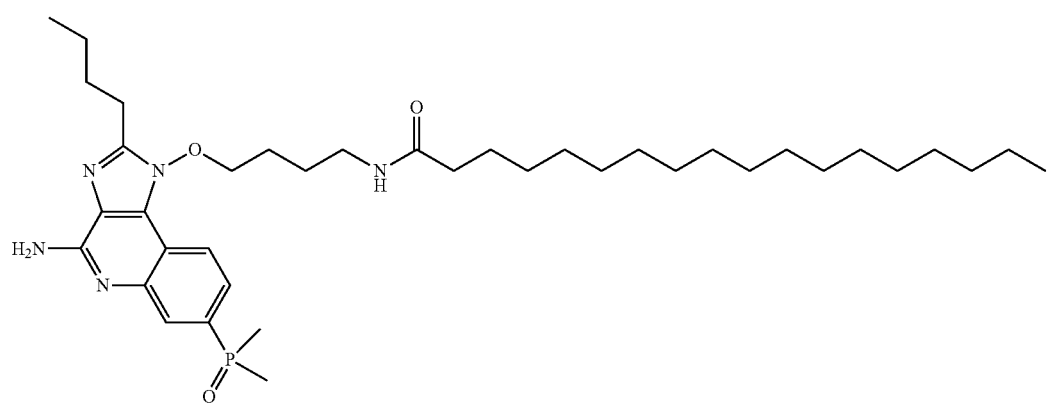 [SMILES: CCCCCCCCCCCCCCCCCC(=O)NCCCCOn1c(CCCC)nc2c(N)nc3cc(P(C)(C)=O)ccc3c21]
3
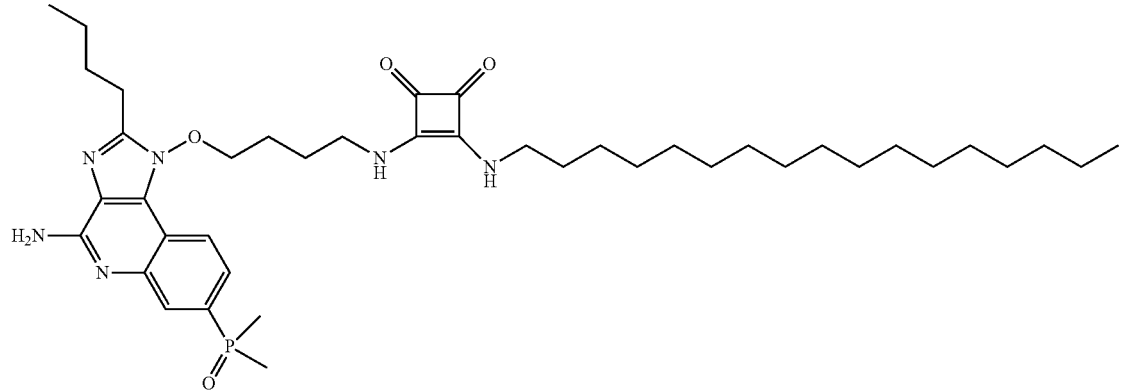 [SMILES: CCCCCCCCCCCCCCCCCNc1c(NCCCCOn2c(CCCC)nc3c(N)nc4cc(P(C)(C)=O)ccc4c32)c(=O)c1=O]
4

TABLE 1-continued
Exemplary Compounds
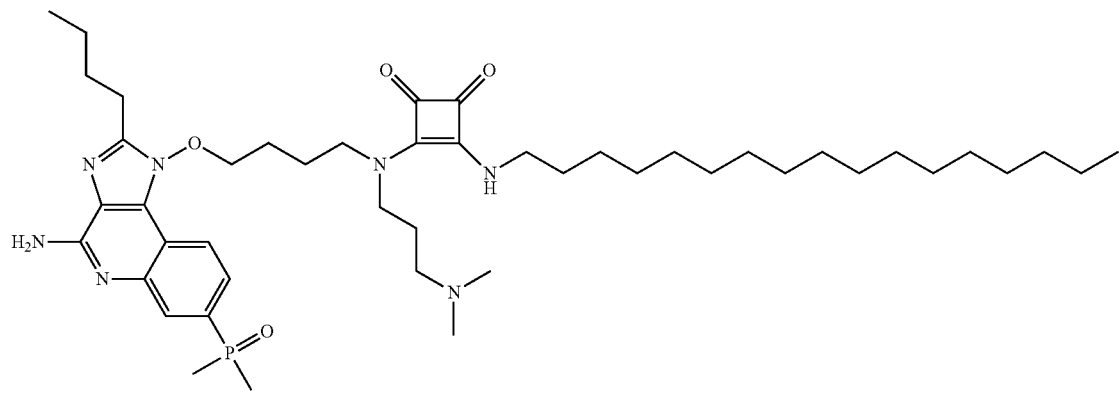 [SMILES: CCCCCCCCCCCCCCCCCNc1c(N(CCCCOn2c(CCCC)nc3c(N)nc4cc(P(C)(C)=O)ccc4c32)CCCN(C)C)c(=O)c1=O]
5
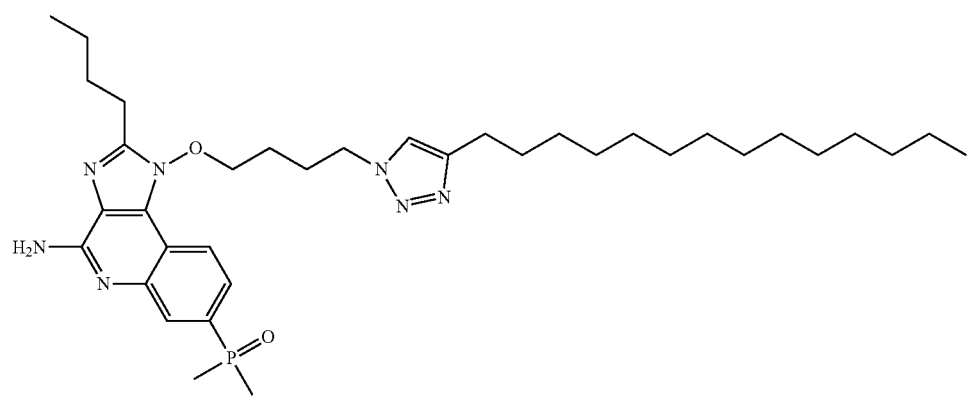 [SMILES: CCCCCCCCCCCCCCc1cn(CCCCOn2c(CCCC)nc3c(N)nc4cc(P(C)(C)=O)ccc4c32)nn1]
6
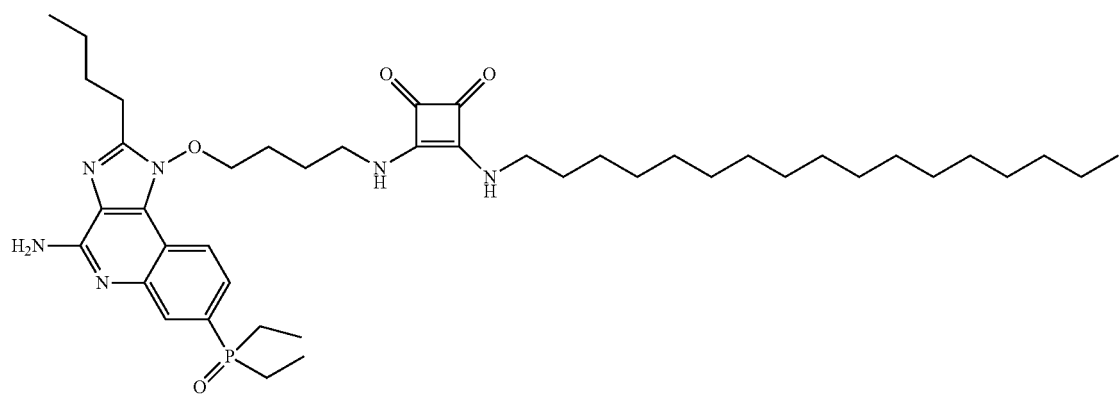 [SMILES: CCCCCCCCCCCCCCCCCNc1c(NCCCCOn2c(CCCC)nc3c(N)nc4cc(P(=O)(CC)CC)ccc4c32)c(=O)c1=O]
7

In certain embodiments, the compound is

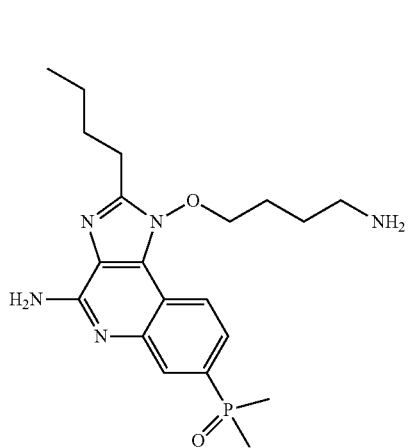

or a pharmaceutically acceptable form or an isotope derivative thereof.

In certain embodiments, the compound is

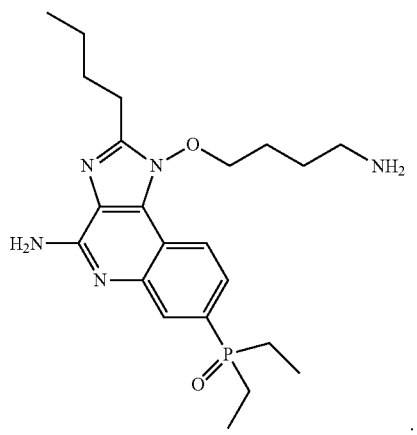 [SMILES: CCCCc1nc2c(N)nc3cc(P(=O)(CC)CC)ccc3c2n1OCCCCN]

or a pharmaceutically acceptable form or an isotope derivative thereof.

In certain embodiments, the compound is

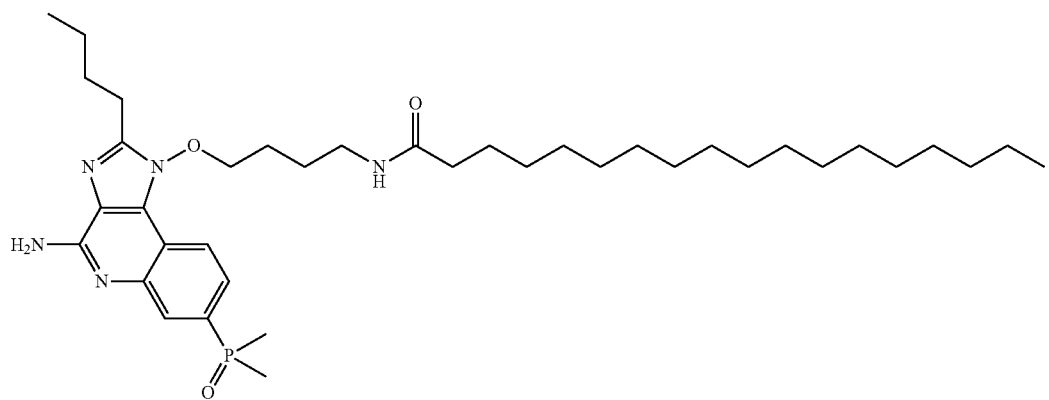

or a pharmaceutically acceptable form or an isotope derivative thereof.

In certain embodiments, the compound is

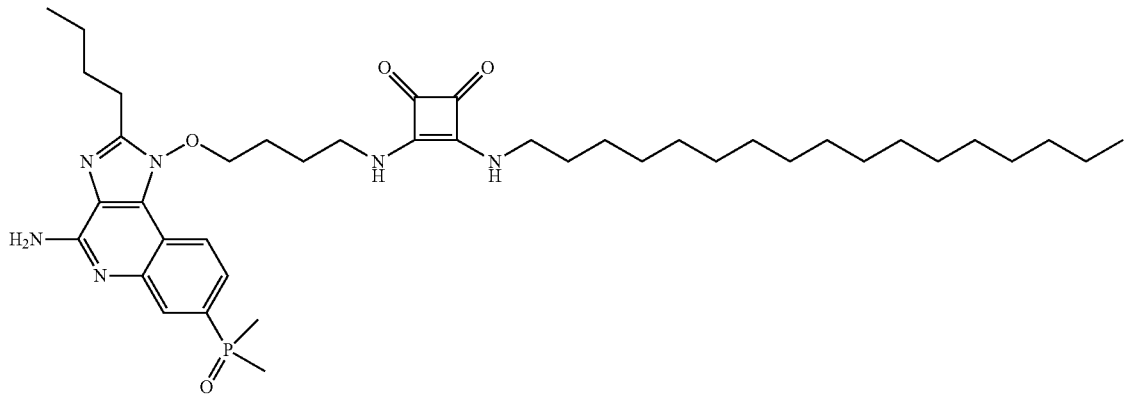

or a pharmaceutically acceptable form or an isotope derivative thereof.

In certain embodiments, the compound is
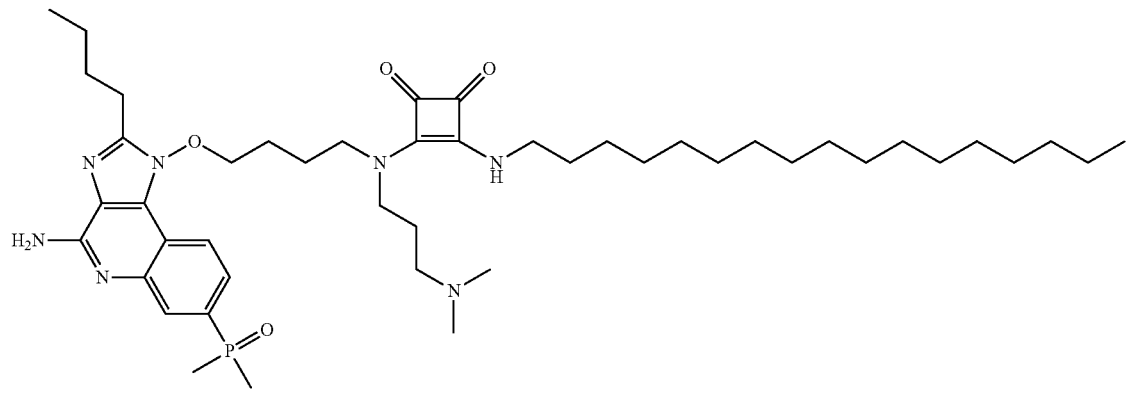
5
or a pharmaceutically acceptable form or an isotope derivative thereof.
In certain embodiments, the compound is
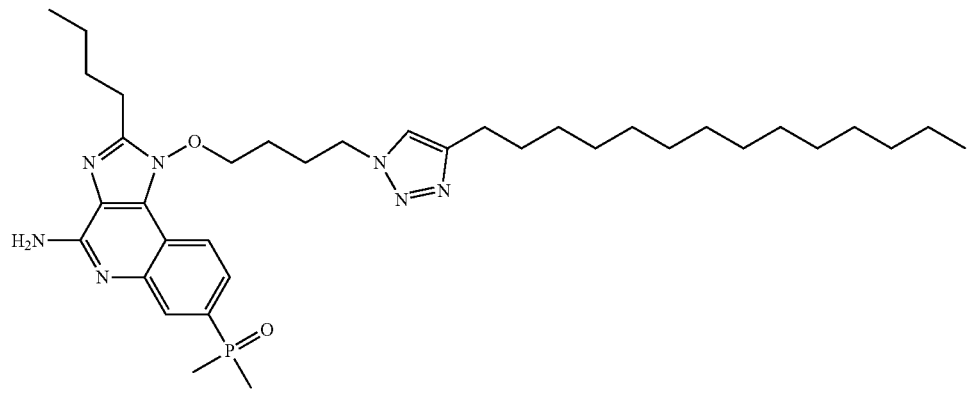 [SMILES: CCCCCCCCCCCCCCc1cn(CCCCOn2c(CCCC)nc3c(N)nc4cc(P(C)(C)=O)ccc4c32)nn1]
or a pharmaceutically acceptable form or an isotope derivative thereof.
In certain embodiments, the compound is
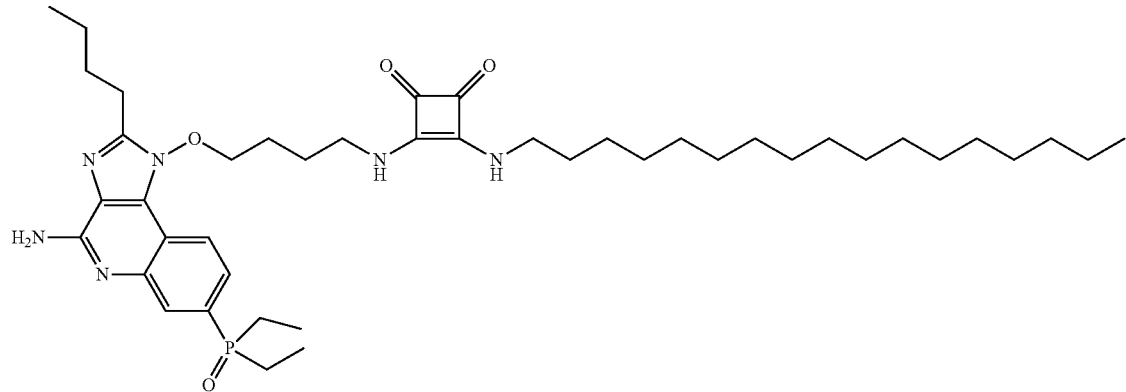
7
or a pharmaceutically acceptable form or an isotope derivative thereof.

In another aspect, the invention generally relates to a pharmaceutical composition comprising a compound disclosed herein.

In yet another aspect, the invention generally relates to a pharmaceutical composition comprising an amount of a compound having the structural formula of (I):

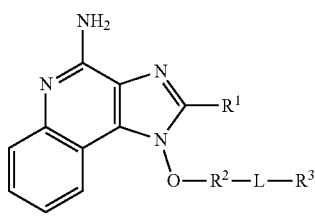

(I)

wherein, $R^1$ is a $C_1$-$C_8$ (e.g., $C_1$-$C_4$, $C_4$-$C_6$, $C_6$-$C_8$) alkyl group;

$R^2$ is $(CH_2)_m$, wherein in is an integer selected from 1 to 8 (e.g., 1, 2, 3, 4, 5, 6, 7, 8);

L is a linking moiety;

$R^3$ is a H, or a $C_1$-$C_{12}$ (e.g., $C_1$-$C_{16}$, $C_{16}$-$C_{32}$, $C_{16}$-$C_{24}$) alkyl group; and or a pharmaceutically acceptable form or an isotope derivative thereof, effective to treat, prevent, or reduce one or more diseases or disorders, in a mammal, including a human, and a pharmaceutically acceptable excipient, carrier, or diluent.

In certain embodiments, the pharmaceutical composition disclosed herein is effective to treat, reduce or prevent an autoimmune disease, or a related disease or disorder.

In certain embodiments, the pharmaceutical composition disclosed herein is effective to treat, reduce or prevent graft rejection, or a related disease or disorder.

In certain embodiments, the pharmaceutical composition disclosed herein is effective to treat, reduce or prevent an allergy, or a related disease or disorder.

In certain embodiments, the pharmaceutical composition disclosed herein is effective to treat, reduce or prevent an immunodeficiency, or a related disease Of disorder.

In certain embodiments, the pharmaceutical composition disclosed herein is effective to treat, reduce or prevent infection, sepsis, or a related disease or disorder.

In certain embodiments, the pharmaceutical composition disclosed herein is effective to treat, reduce or prevent cancer, or a related disease or disorder.

In yet another aspect, the invention generally relates to a unit dosage form comprising a compound disclosed herein.

In yet another aspect, the invention generally relates to a unit dosage form comprising a pharmaceutical composition disclosed herein.

In yet another aspect, the invention generally relates to a method for treating, reducing, or preventing a disease or disorder, comprising administering to a subject in need thereof a pharmaceutical composition comprising a compound having the structural formula of

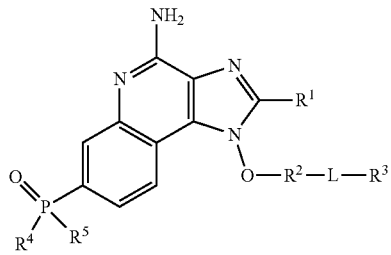

(I)

wherein, $R^1$ is a $C_1$-$C_8$ alkyl group;

$R^2$ is $(CH_2)_m$, wherein m is an integer selected from 1 to 8;

L is a linking moiety;

$R^3$ is H, or $C_1$-$C_{32}$ alkyl group; and each of $R^4$ and $R^5$ is independently a $C_1$-$C_6$ aliphatic group; provided that $R^4$ and $R^5$, together oath atoms to which they are bonded to, may optionally form a 5- to 7-membered aliphatic ring, or a pharmaceutically acceptable form or an isotope derivative thereof effective to treat, prevent, or reduce one or more of autoimmune diseases, graft rejection, allergies, immunodeficiency, infection, sepsis, cancer, or a related disease or disorder thereof, in a mammal, including a human, and a pharmaceutically acceptable excipient, carrier, or diluent.

In certain embodiments, the method is to treat, reduce or prevent an autoimmune disease, or a related disease or disorder.

In certain embodiments, the method is to treat, reduce or prevent graft rejection, or a related disease or disorder.

In certain embodiments, the method is effective to treat, reduce or prevent allergy, or a related disease or disorder.

In certain embodiments, the method is effective to treat, reduce or prevent an immunodeficiency, or a related disease or disorder.

In certain embodiments, the method is effective to treat, reduce or prevent infection and/or sepsis, or a related disease or disorder.

In certain embodiments, the method is effective to treat, reduce or prevent cancer, or a related disease or disorder.

In yet another aspect, the invention generally relates to a method for modulating immune response, comprising administering to a subject in need thereof a pharmaceutical composition comprising a compound disclosed herein.

In yet another aspect, the invention generally relates to a method for modulating TLR7- and/or TLR8-mediated signaling, comprising administering to a subject in need thereof a pharmaceutical composition comprising a compound disclosed herein.

In yet another aspect, the invention generally relates to a method for of treating or reducing a condition or disorder treatable by modulation of TLR7- and/or TLR8-mediated cellular activities, comprising administering to a subject in need thereof a pharmaceutical composition comprising a compound disclosed herein.

In yet another aspect, the invention generally relates to a method for treating, reducing, or preventing a disease or disorder, comprising administering to a subject in need thereof a pharmaceutical composition comprising a compound disclosed herein, wherein the disease or disorder is autoimmune diseases, graft rejection, allergies, immunodeficiency, infection, sepsis, cancer, or a related disease or disorder.

In certain embodiments, the compound is an agonist of TLR7.

In certain embodiments, the compound is an agonist of TLR8.

In yet another aspect, the invention generally relates to use of a compound disclosed herein for treating, reducing or preventing a disease or disorder.

In yet another aspect, the invention generally relates to use of a compound disclosed herein and a pharmaceutically acceptable excipient, carrier, or diluent, in preparation of a medicament for treating, reducing or preventing a disease or disorder.

In certain embodiments, the disease or disorder is mediated by or associated with TLR7- and/or TLR8-mediated signaling.

In certain embodiments, the compound disclosed herein is used to treat, reduce or prevent a disease or disorder selected from autoimmune diseases, graft rejection, allergies, immunodeficiency, infection, sepsis, cancer, or a related disease or disorder thereof.

In certain embodiments, the compound disclosed herein is used to treat, reduce or prevent an autoimmune disease, or a related disease or disorder.

In certain embodiments, the compound disclosed herein is used to treat, reduce or prevent graft rejection, or a related disease or disorder.

In certain embodiments, the compound disclosed herein is used to treat, reduce or prevent allergy, or a related disease or disorder.

In certain embodiments, the compound disclosed herein is used to treat, reduce or prevent immunodeficiency, or a related disease or disorder.

In certain embodiments, the compound disclosed herein is used to treat, reduce or prevent infection anchor sepsis, or a related disease or disorder.

In certain embodiments, the compound disclosed herein is used to treat, reduce or prevent cancer, or a related disease or disorder.

The compounds according to the invention may be used as agonists of TLR's, specifically for TLR7 and TLR8.

The compounds according to the invention may provide methods for modulating TLR7- and/or TLR8-mediated signaling. The methods of the invention are useful, for example, when it is desirable to alter TLR7- and/or TLR8-mediated signaling in response to a suitable TLR7 and/or TLR8 ligand or a TLR7 and/or TLR8 signaling agonist.

The compounds according to the invention may be used in the treatment or prevention of conditions and disorders include, but are not limited to, cancer, immune complex-associated diseases, inflammatory disorders, immunodeficiency, graft rejection, graft-versus-host disease, allergies, asthma, infection, and sepsis. More specifically, methods useful in the treatment of conditions involving autoimmunity, inflammation, allergy, asthma, graft rejection. Alternatively, methods useful in the treatment of conditions involving infection, cancer, and immunodeficiency generally will employ compounds disclosed herein that augment TLR7- and TLR8-mediated signaling in response to a suitable TLR7 and/or TLR8 ligand. In some instances, the compositions can be used to inhibit or promote TLR 7- and/or TLR8-mediated signaling in response to a TLR7 and/or TLR8 ligand or signaling agonist in other instance, the compositions can be used to inhibit or promote TLR7- author TLR8-mediated immune-stimulation in a subject.

The compounds according to the inventions may also be used in the treatment or prevention of hepatocarcinomas, cholangiocarcinoma and malignant mesothelioma, pancreatic cancer, head and neck cancer, and haemoangioma.

The compounds according to the inventions may also be used in the treatment or prevention treating obesity in a patient. The invention provides a method of treating type II diabetes in a patient in need of treatment comprising administering to the patient an effective amount of a compound disclosed herein or a pharmaceutically acceptable salt thereof. Preferably the patient is a human. The present invention provides a method for treating nonalcoholic steatohepatitis in a patient in need of such treatment, comprising administering to the patient an effective amount of a compound disclosed herein or a pharmaceutically acceptable salt thereof.

The present invention provides use of a compound disclosed herein, or a pharmaceutically acceptable salt thereof, in the manufacture of a medicament for the treatment of obesity. The present invention provides the use of a compound disclosed herein, or a pharmaceutically acceptable salt thereof, in the manufacture of a medicament for treatment to provide therapeutic weight loss.

The amount of compound in compositions of this invention is such that is effective to measurably modulate TLR's, in particular TLR7 and/or TLR8, or a mutant thereof, in a biological sample or in a patient. In certain embodiments, the amount of compound in compositions of this invention is such that is effective to measurably modulate TLR's, or a mutant thereof, in a biological sample or in a patient. In certain embodiments, a composition of this invention is formulated for administration to a patient in need of such composition.

Solid dosage forms for oral administration include capsules, tablets, pills, powders, and granules, in such solid dosage forms, the compounds described herein or derivatives thereof are admixed with at least one inert customary excipient (or carrier) such as sodium citrate or dicalcium phosphate or (i) tillers or extenders, as for example, starches, lactose, sucrose, glucose, mannitol, and silicic acid, (ii) binders, as for example, carboxymethylcellulose, alginates, gelatin, polyvinylpyrrolidone, sucrose, and acacia, (iii) humectants, as for example, glycerol, (iv) disintegrating agents, as for example, agar-agar, calcium carbonate, potato or tapioca starch, alginic acid, certain complex silicates, and sodium carbonate, (v) solution retarders, as for example, paraffin, (vi) absorption accelerators, as for example, quaternary ammonium compounds, (vii) wetting agents, as for example, cetyl alcohol, and glycerol monostearate, (viii) adsorbents, as for example, kaolin and bentonite, and (ix) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents. Solid compositions of a similar type may also be employed as fillers in soft and hard-filled gelatin capsules using such excipients as lactose or milk sugar as well as high molecular weight polyethyleneglycols, and the like. Solid dosage forms such as tablets, dragees, capsules, pills, and granules can be prepared with coatings and shells, such as enteric coatings and others known in the art.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, such as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfaryl alcohol, polyethyleneglycols, and fatty acid esters of sorbitan, or mixtures of these substances, and the like. Besides such inert diluents, the composition can also include additional agents, such as wetting, emulsifying, suspending, sweetening, flavoring, or perfuming agents.

Materials, compositions, and components disclosed herein can lie used for, can be used in conjunction with, can be used in preparation for, or are products of the disclosed methods and compositions. It is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Compositions of the present invention are administered orally, parenterally, by inhalation spray, topically, rectally, nasally, buccally, vaginally or via an implanted reservoir . . . The term "parenteral" as used herein includes subcutaneous, intravenous, intramuscular, intra-articular, intra-synovial, intrasternal, intrathecal, intrahepatic, intralesional, intratumoral and intracranial injection or infusion techniques.

Pharmaceutically acceptable compositions of this invention are orally administered in any orally acceptable dosage form. Exemplary oral dosage forms are capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents are optionally also added.

Alternatively, pharmaceutically acceptable compositions of this invention are administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention are also administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches are also used.

For topical applications, provided pharmaceutically acceptable compositions are formulated in a suitable ointment containing the active component suspended or dissolved in one or more carriers. Exemplary carriers for topical administration of compounds of this are mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Pharmaceutically acceptable compositions of this invention are optionally administered by nasal aerosol or inhalation. Such compositions are prepared according to techniques well-known in the art of pharmaceutical formulation and are prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food . . . In some embodiments, pharmaceutically acceptable compositions of this invention are administered without food. In other embodiments, pharmaceutically acceptable compositions of this invention are administered with food.

The amount of compounds of the present invention that are optionally combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to as patient receiving these compositions.

It should also be understood that a specific dosage and treatment regimen for any particular patient will depend upon a variety of factors, including the activity of the specific compound employed, the age, body weight, general health sex, diet, time of administration, rate of excretion, drug combination, and the judgment of the treating physician and the severity of the particular disease being treated. The amount of a compound of the present invention in the composition will also depend upon the particular compound in the composition.

The following examples are meant to be illustrative of the practice of the invention and not limiting in any way.

EXAMPLES

The below Examples describe certain exemplary embodiments of compounds prepared according to the disclosed invention. It will Be appreciated that the following general methods, and other methods known to one of ordinary skill in the art, can be applied to compounds and subclasses and species thereof, as disclosed herein.

¹H NMR was recorded on a Bruker 400 MHz spectrometer, using residual signal of deuterated solvent as internal reference. Chemical shifts (δ) are reported in ppm relative to the residual solvent signal (δ=2.50 ppm for 1H NMR in DMSO-d6; δ=3.31 ppm for 1H NMR in MeOD-d4).

LCMS was taken on a quadrupole Mass Spectrometer on Shimadzu LC/MS2020 Series (SunFire C18 3.5 μm 50*4.6 mm) operating in ES (+) or (−) ionization mode; T=40° c., flow rate=2.0 mL/min; detected wavelength: 254 nm.

HPLC was performed under conditions: (Flash; Welchrom C18 5 μm 4.6×150 min); Wavelength 254 am and 214 nm; Mobile phase: A water (0.03% TFA); B (0.03% TFA); Flow rate: 1 ml/min; Injection volume: 2 μL; Run time: 16 min; Equilibration: 6 min.

Prep-HPLC was performed under conditions: (Flash: Welchrom C18 250×19 mm); Wavelength 254 nm; and 214 nm; Mobile phase: A water (0.1% HCl):, B MeCN; Flow rate: 20 mL/min; Injection volume: 0.5 mL; Run time: 18 min; Equilibration: 2 min.

Example 1

(4-amino-1-(4-aminobutoxy)-2-butyl-1)1H-imidazo[4,5-c]quinolin-7-yl)dimethylphosphine Oxide (I)

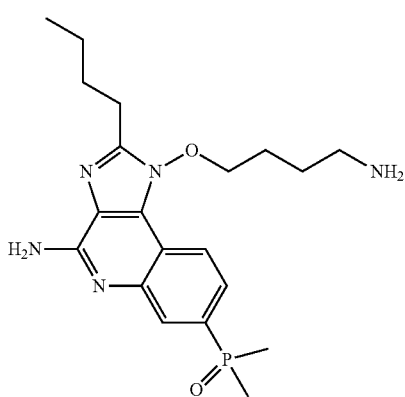

Scheme 1

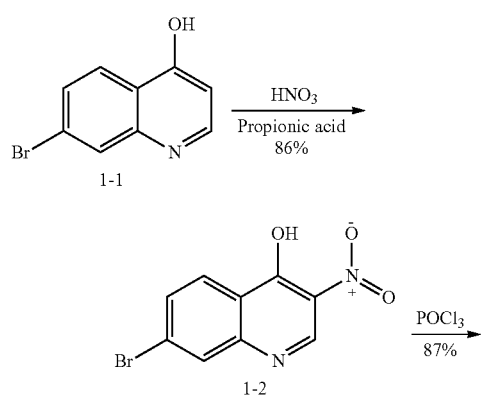

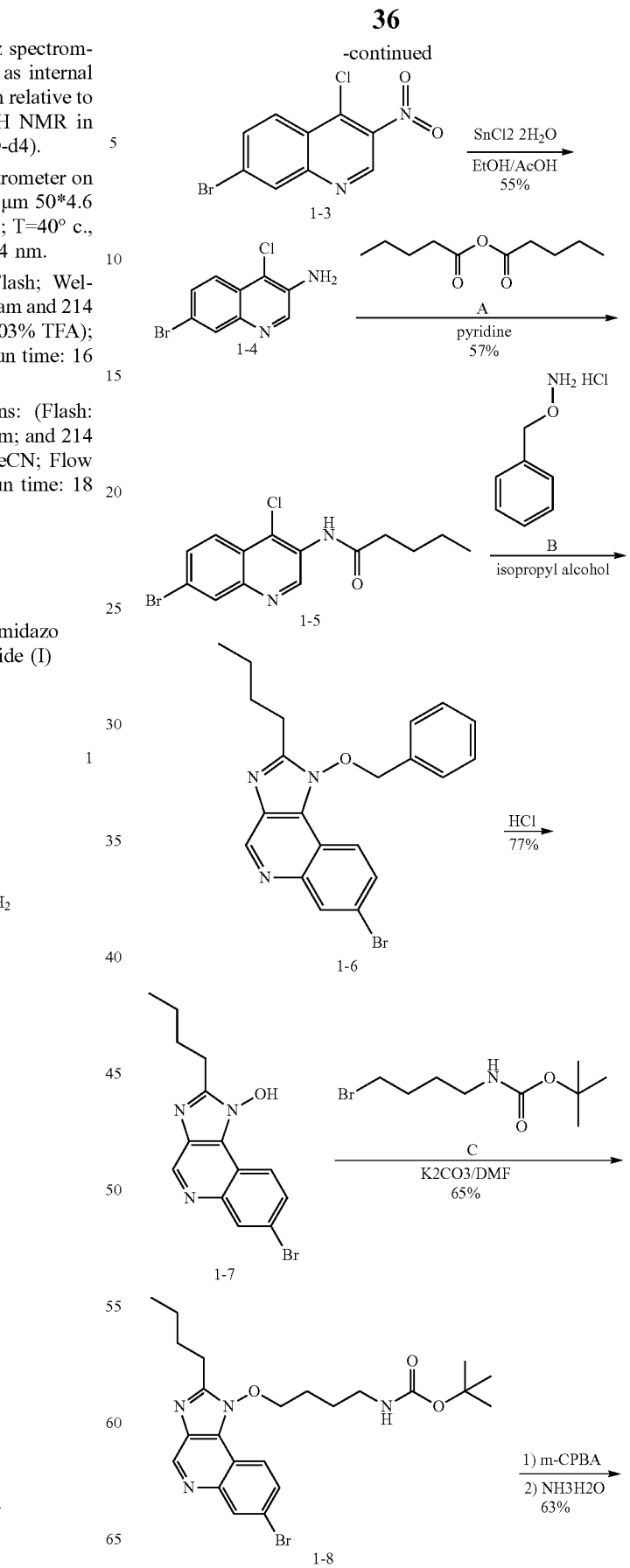

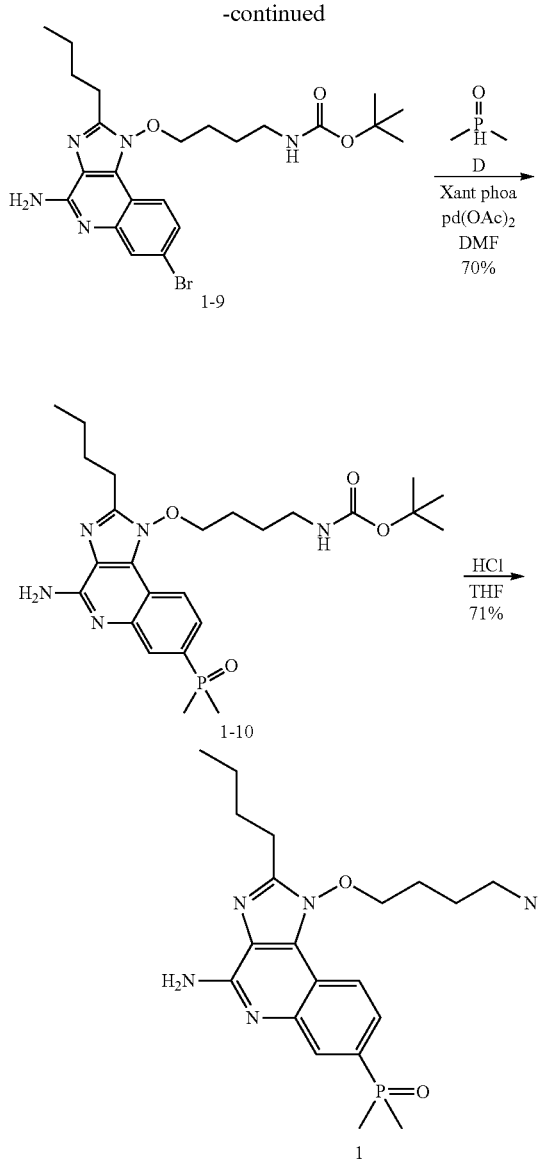

Step 1. Synthesis of 7-bromo-3-nitroquinolin-4-ol (1-2)

To a solution of compound 1-1 (10.0 g, 45.0 mol) in propionic acid (80 mL) was added nitric acid (5.0 mL, 70%) at rt. The reaction mixture was heated to 130° C. overnight. The reaction mixture was cooled to room temperature and filtered. The resulting solid was washed with water (50 mL×3) and dried in vacuum to give compound 1-2 (8.6 g, yield: 66%) as a yellow solid. NMR (400 MHz, DMSO-d$_6$): δ10.91 (s, 1H), 8.68 (s, 1H), 7.91-7.89 (d, 8 Hz, 1H), 6.97-6.94 (d, 8.8 Hz, 1H), 6.87-6.86 (d, J=2.4 Hz, 1H). LCMS [mobile phase: from 100% water (0.02% NH$_4$Ac) to 5% water (0.02% NH$_4$Ac) and 95% CH$_3$CN in 2.5 min]: Rt=0.85 min, MS Calcd.: 267.9 MS Found: 269.2 ([M+H]$^+$).

Step 2: Synthesis of 7-bromo-4-chloro-3-nitroquinoline (1-3)

To a solution of compound 1-2 (8.8 g, 33.0 mmol) was in POCl$_3$ (25 mL) was added anhydrous DMF (1 mL). The reaction mixture was heated to 85° C. under nitrogen overnight. The reaction mixture was cooled to room temperature. The precipitate was collected by filtration, washed with water and dried in high vacuum to give compound 1-3 (8.0 g, yield: 87%) as a yellow solid. $^1$H NMR (400 MHz, DMSO): δ9.30 (s, 1H), 8.44-8.42. (d, 8 Hz, 1H), 8.04-8.02. (d, J=8 Hz, 1H) 7.26 (s, 1H).

Step 3: Synthesis of 7-bromo-4-chloroquinlin-3-amine -4)

To a solution of compound 1-3 (8.0 g, 27.7 mmol) in EtOH (50 mL) and AcOH (10 mL) was added SnCl$_2$.2H$_2$O (18.7 g, 83.3 mmol) as one portion. The reaction mixture was then refluxed for 5 hours. The reaction mixture was cooled to 0° C. and the pH was adjusted to basic with saturated NaHCO$_3$. The mixture was extracted with DCM (100 mL×3). The combined organic layers were dried over Na$_2$SO$_3$, filtered and concentrated. The residue was triturated with Et$_2$O to give compound 1-4 (4.0 g, yield: 55%) as a yellow solid. LCMS: [mobile phase: from 100% water (0.02% NH$_4$Ac to 5% water (0.02% NH$_4$Ac) and 95% CH$_3$CN in 2.5 min] Rt=1.55 min, MS Calcd.: 255.9 MS Found: 2571 ([M+H]$^+$).

Step 4: Synthesis of N-(7-bromo-4-chloroquinolin-3-yl) pentanamide (1 -5)

To a solution of compound A (3.3 g, 17.8 mmol) in pyridine (4.0 mL) was added compound 1-4 (3.8 g, 14.8 mmol). The reaction mixture was stirred at room temperature for 2 hours. The solvent was evaporated in vacuum. The residue was purified by column chromatography on silica gel (DCM/MeOH=50:1) to give compound 1-5 (2.9 g, yield: 57%) as a yellow solid. $^1$H NMR (400 MHz, DMSO-d$_6$): δ9.44 (s, 8.68-8.66 (d, 8 Hz, 1H), 8.48-8.45 (s, 1H), 7.42 (s, 1H), 3.05-2.99 (m, 2H), 1.88-1.82 (m, 2H), 1.47-1.40 (m, 2H), 0.97-0.93 (m, 3H), LCMS: [mobile phase: from 100% water (0.02% NH$_4$Ac) to 5% water (0.02% NH$_4$Ac) and 95% CH$_3$CN in 2.5 min] Rt=1.71 min, MS Calcd.: 340.0 MS Found: 341.2 ([M+H]$^+$)

Step 5: Synthesis of 1-(benzyloxy)-7-bromo-2-butyl-1H-imidazo [4,5-c]quinoline (1-6)

A solution of compound 1-5 (2.9 g, 8.5 mmol) and compound B (2.0 g, 12.8 mmol) in isopropyl alcohol (50 mL) was heated at reflux overnight. The reaction mixture was cooled to rt and concentrated under reduced pressured to give compound 1-6 (2.0 g, crude) which was used to the next step without further purification LCMS [mobile phase: from 100% water (0.02% NH$_4$Ac) to 5% water (0.02% NH$_4$Ac) and 95% CH$_3$CN in 2.5 min] Rt=1.987 min; MS Calcd.: 409.1 MS Found: 410.1 ([M+H]$^+$).

Step 6: Synthesis of 7-bromo-2-butyl-1H-imidazo [4,5-c] quinolin-1-ol (1-7)

A solution of compound. 1-6 (300 mg, 0.73 mmol) in conc. HCl (5 mL) was stirred at rt overnight. The reaction mixture was cooled to 0° C. and the pH was adjusted to basic with saturated NaHCO$_3$. The mixture was extracted with DCM (20 mL×3). The combined organic layer was dried over Na$_2$SO$_3$, filtered and concentrated to give compound 1-7 (180 mg, yield: 77%) as a yellow solid. LCMS: [mobile phase: from 100% water (0.02% NH$_4$Ac) to 5% water (0.02% NH$_4$Ac)and 95% CH$_3$CN in 2.5 min] Rt=1.38 min; MS Calcd.: 319.0 MS Found. 320.2 ([N+H]$^+$).

Step 7: Synthesis of tert-butyl (4-((7-bromo-2-butyl-1H-imidazo [4,5-c]quinotin-1-yl)oxy)butyl)carbamate (1-8)

To a solution of compound 1-7 (200 mg, 0.63 mmol) in DMF (5 mL) was added compound C (190 mg, 0.76 mmol)

and K$_2$CO$_3$ (260 mg, 1.89 mmol). The reaction mixture was stirred at rt overnight. The solvent was evaporated in vacuum. The residue was purified by column chromatography on silica gel (PE/EA=3:1) to give compound 1-8 (200 mg, yield: 65%) as yellow oil. $^1$H NMR (400 MHz, CDCl$_3$): δ9.21 (s. 1H), 8.42 (d, J=2.0 Hz, 1H), 8.18-8.16 (d, J=8.8 Hz, 1H), 7.76 (d, 8.8 Hz, 1H), 4.33 (t, J=6.4 Hz, 2H), 3.00 (t, J=6.4 Hz, 2H), 2.04-1.93 (m, 4H), 1.54-1.50 (m, 2H), 1.49 (s, 1H), 1.03-0.99 (t, J=8 Hz, 3H). LCMS: [mobile phase: from 100% water (0.02% NH$_4$Ac) to 5% water (0.02% NH$_4$Ac) and 95% CH$_3$CN in 2.5 min] Rt=1.71 min; MS Calcd.: 340.0 MS Found: 341.2 ([M+H]$^+$).

Step 8: Synthesis of tert-butyl (4-((4-amino-7-bromo-2-butyl-1H-imidazo[4,5-c]quinolin-1-yl)oxy)butyl)carbamate (1-9)

To a stirred solution of compound 1-8 (1.5 g, 3.0 mmol) in DCM (50 mL) was added m-CPBA (1.2 g, 6.0 mmol). The reaction mixture was stirred for 2 hours. To the reaction mixture was added concentrated NH$_3$H$_2$O (2.0 mL) at 0° C. The solvent was evaporated in vacuum and the residue was purified by column chromatography on silica gel (PETA=1:1) to give compound 1-9 (800 mg, yield: 53%) as a white solid, LCS: [mobile phase: from 100% water (0.02% NH$_4$Ac) to 5% water (0.02% NH$_4$Ac) and 95% CH$_3$CN in 2.5 min] Rt=1.598 min; MS Calcd.: 505.1 MS Found: 507.2 ([M+H]$^+$).

Step 9: Synthesis of tert-butyl (4-((4-amino-2-butyl-7-(dimethylphosphoryl)-1H-imidazo[4,5-c]quinolin-1-yl)oxy)butyl)carbamate (1-10)

To a stirred mixture of compound 1-9 (500 mg, 1.0 mmol) and compound D (390 mg, 5.0 mmol) in DMF (10 mL) was added Xant phos (58 mg, 0.1 mmol) and Pd(OAc)$_2$ (23 mg, 0.1 mmmol). The reaction mixture was stirred at 130° C. for 2 hours in microwave under N$_2$. The reaction mixture was cooled to rt was evaporated in vacuum and the residue was purified by prep-HPLC to give compound 10 (350 mg, yield: 70%) as a white solid. LCMS: [mobile phase: from 100% water (0.02% NH$_4$Ac) to 5% water (0.02% NH$_4$Ac) and 95% CH$_3$CN in 2.5 min] Rt=1.48 min; MS Calcd.: 503.2 MS Found: 504.4 ([M+H]$^+$)

Step 10: Synthesis of (4-amino-1-(4-aminobutoxy)-2-butyl-1H-imidazo[4,5-c]quinolin-7-yl)dimethylphosphine oxide (1)

To a solution of compound 1-10 (350 mg, 0.7 mmol) in THF (5 mL) was added con. HCl (3 mL). The reaction mixture was stirred at rt for 3 hours. The solvent was evaporated in vacuum and the residue was purified by prep-HPLC to give compound 1 (200 mg, yield: 71%) as a white solid. $^1$HNMR (400 MHz, DMSO-d$_6$) δ8.15-8.13 (m, 1H), 7.98-7.94 (m, 1H), 7.61 (t, J=9.6 Hz, 1H), 6.78 (s, 1H), 4.36-4.33 (m, 2H), 3.07-3.05 (m, 1H), 2.98-2.94 (m, 2H), 2.68-2.65 (m, 1H), 1.95-1.79 (m, 4H), 1.72 (s, 3H), 1.70 (s, 3H), 1.69-1.62 (m, 2H), 1.47-1.41 (m, 2H), 0.97-0.93 (m, 3H) LCMS: [mobile phase: from 80% water (0.02% NH$_3$Ac) and 20% CH$_3$CN to 5% water (0.02% NH$_4$Ac) and 95% CH$_3$CN in 6 min] purity=93.1%, Rt=2.64 min; MS Calcd.: 403.4 MS Found: 404.2 ([M+H]$^+$).

Example 2

(4-amino-1-(4-aminobutoxy)-2-butyl-1H-imidazo[4,5-c]quinolin-7-yl)diethylphosphine oxide (2)

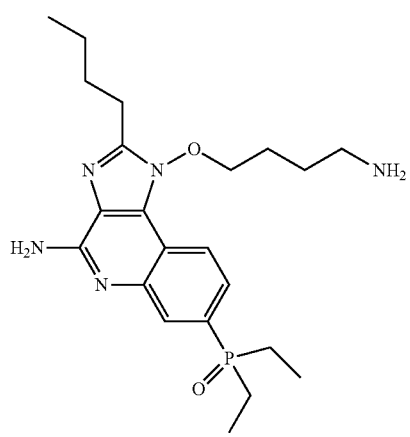

2

Scheme 2

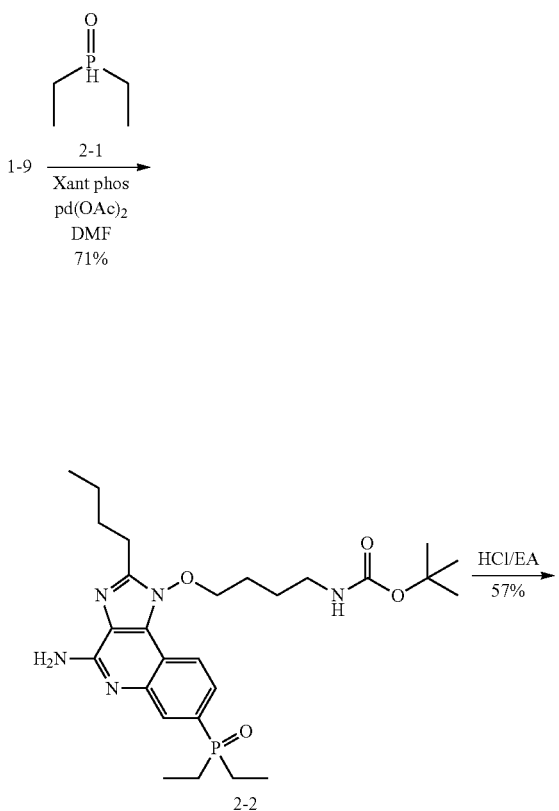

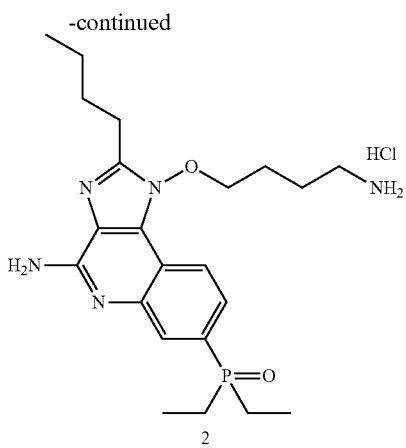

Step 1: To a stirred mixture of compound 1-9 (600 mg, 1.2 mmol) and diethylphosplin e oxide 2-1 (636 mg, 6.0 mmol) in DMF (10 mL) was added Xant phos (69 mg, 0.12 mmol) and Pd(OAc)$_2$ (27 mg, 0.12 mmol). The reaction mixture was stirred at 130° C. for 2 hrs under the condition of microwave. The mixture was concentrated in vacuum and the residue was purified by chromatography on a silica column (DCM/MeOH=20:1, v/v) to give compound 2-2 (450 mg, yield: 71%) as a yellow solid.

Step 2: A solution of compound 2-2 (400 mg, 0.75 mmol) in HCl/EA (10 mL) was stirred at rt for 5 hrs. The solvent was evaporated in vacuum to give compound compound 2 (200 mg, yield: 57%) as a yellow solid. This solid was dissolved in the water and extracted with ethyl acetate. The resulting aqueous was lyophilized to give 100 mg of pure product 2. $^1$HNMR (400 MHz, CD$_3$OD) δ8.44 (dd, J=8.4, J=2.4 Hz, 1H), 8.23-8.20 (d, J=11.6 Hz, 1H), 7.98 (t, J=8.8 Hz, 1H), 4.53 (t, J=5.2 Hz, 2H), 3.12-3.07 (m, 4H), 2.28-2.10 (m, 6H), 2.02-1.93 (m, 4H), 1.60-1.49 (m, 2H), 1.17-1.09 (m, 6H), 1.03(t, J=7.2 Hz, 1H). LCMS purity=96.1%, Rt=3.66 min; MS Calcd.: 404.4 MS Found: 404.3.

Example 3

N-(4-((4-amino-2-butyl-7-(dimethylphosphoryl)-1H-imidazo[4,5-c]quinolin-1-yl)oxy)butyl)stearamide (3)

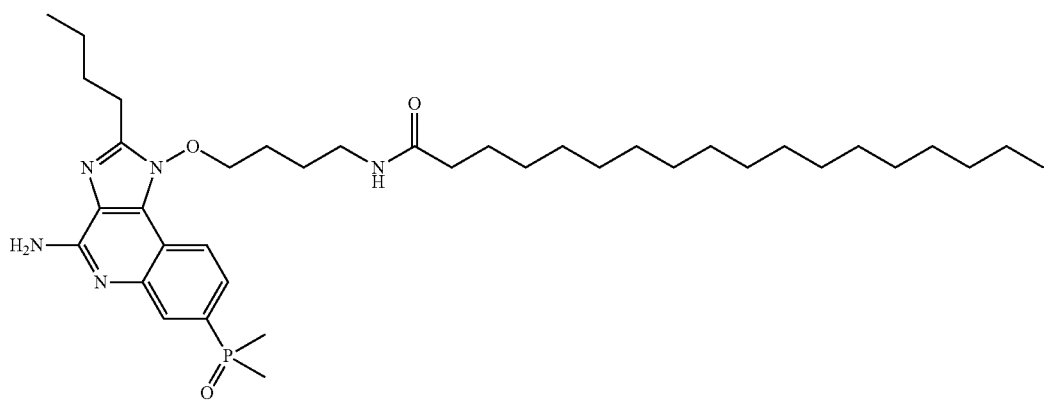

Scheme 3

To a solution of compound 1 (20 mg, 0.05 mmol) in pyridine (10 mL) was added alkyl chlorides (10 mL) and 1 mg of DMAP. The reaction mixture was stirred at it for 2 hours. The solvent was evaporated in vacuum and the residue was purified by prep-HPLC to give compound 3 (20.7 mg, yield 62%) as a yellow oil, $^1$HNMR (400 MHz, DMSO-d$_6$) δ8.20-8.18 (m, 1H), 8.01-7.98 (d, 1H), 5.90-5.77 (m, 2H), 4.31 (s, 1H), 3.51-3.49 (m, 2H), 2.95-2.93 (m, 2H), 2.22-2.18 (m, 2H), 2.01-2.00 (m, 2H), 1.93-1.90 (m, 2H), 1.87 (s, 3H), 1.81 (s, 3H) 1.64-1.62 (m, 2H), 1.51-1.37 (m, 2H) 1.33-1.24 (m, 30H), 1.11-1.08 (m, 3H), 1.02-0.98 (m, 3H), LCMS: [mobile phase: from 80% water (0.02% NH$_4$Ac) and 20% CH$_3$CN to 5% water (0.02% NH$_4$Ac) and 95% CH$_3$CN in 6 min] purity=96.0%, Rt=1.764 min, MS Calcd.: 699.9 MS Found: 670.5 ([M+H]$^+$).

Example 4

N-(4-((4-amino-2-butyl-1H-imidazo[4,5-c]quinolin-1-yl)oxy)butyl)-hexadecylpiperidine-4-carboxamide (4)

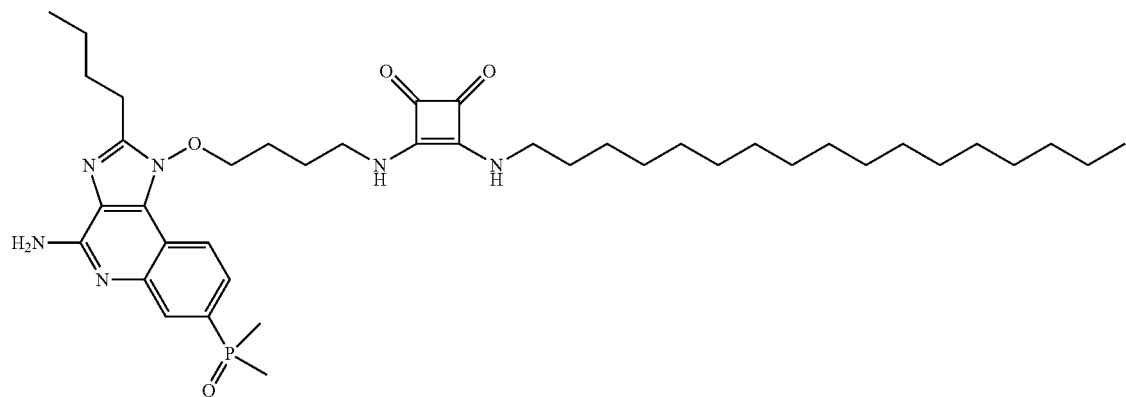

Scheme 4

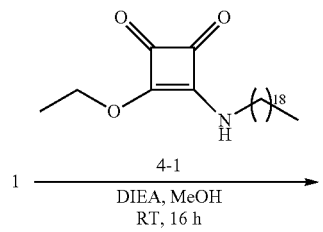

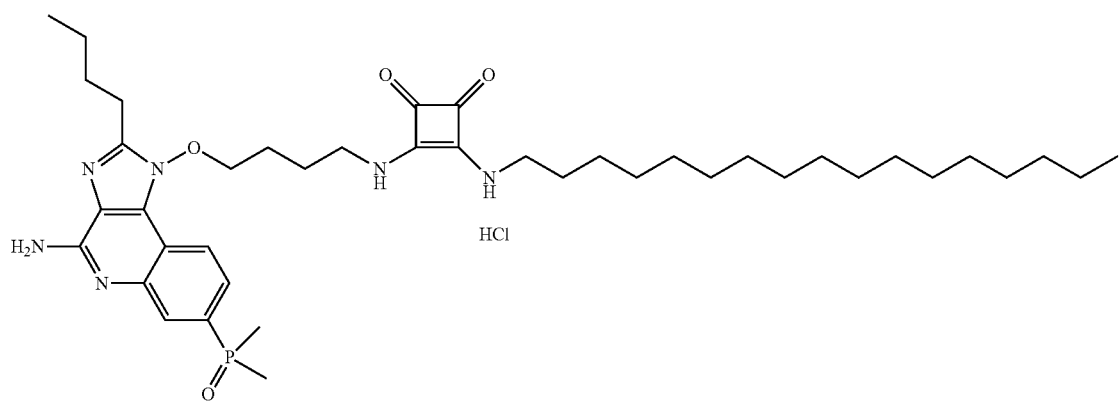

To a solution of 1 (25 mg, 0.062 mmol) and 4-1 (35.3 mg, 0.093 mmol) in MeOH (10 mL) was added DIEA (16.0 mg, 0.124 mmol). The mixture was stirred at room temperature for 16 hours. The mixture was concentrated in vacuo and the residue was purified by prep-HPLC (HCl) to give 4 (HCl salt, 20.57 mg, yield: 50.6%) as a white solid. $^1$H NMR (400 MHz, CDCl$_3$) δ8.71-8.39 (m, 4H), 8.16 (d, J=7.2 Hz, 1H), 8.04 (d, J=11.6 Hz, 1H), 7.72 (t, J=8.8 Hz, 1H), 4.63-4.38 (m, 6H), 3.77-3.65 (m, 4H), 2.99-2.90 (m, 2H), 2.13-2.05 (m, 2H), 1.88 (d, J=13.0 Hz, 6H), 1.67-1.60 (m, 2H), 1.49-1.43 (m, 2H), 1.30-1.20 (m, 28H), 0.97 (t, J=7.2 Hz, 3H), 0.86 (t, J=6.8 Hz, 3H). MS m/z (ESI): 738.0 [M+H]$^+$.

Example 5
N-(4-((4-amino-2butyl-1H-imidazo[4,5-c]quinolin-yl)oxy)butyl)-N3,N3-dimethyl-N1-octadecylpropane-1,3-diamine (5)
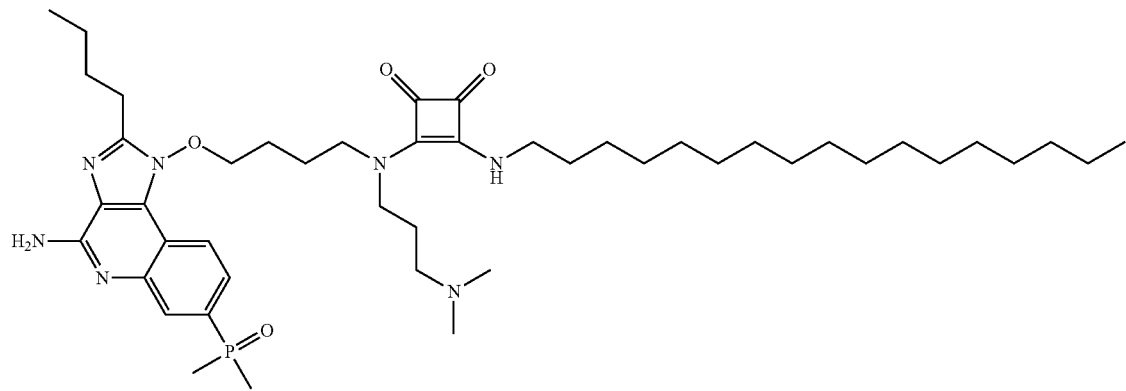
Scheme 5
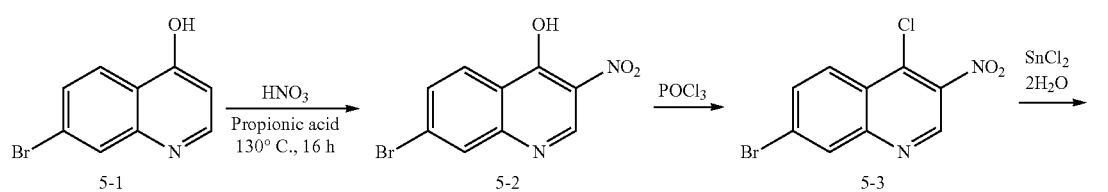
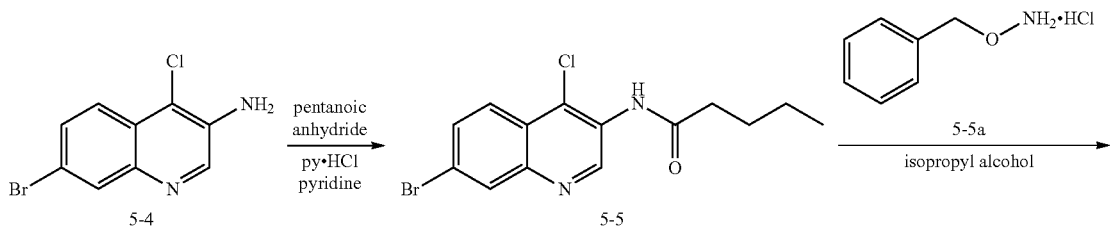
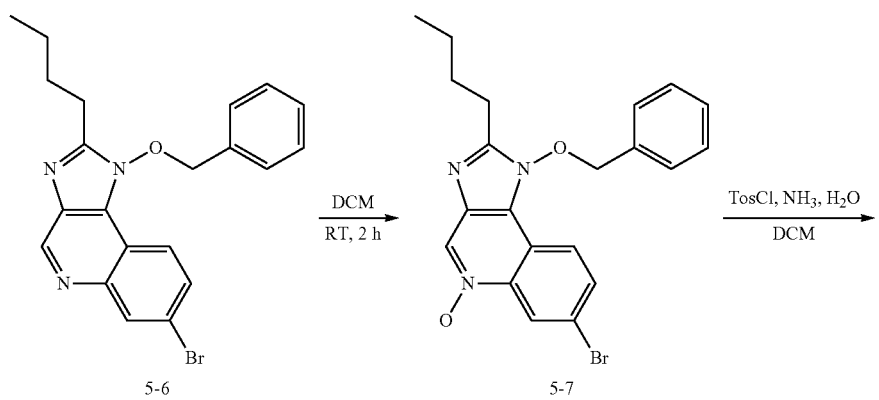

-continued
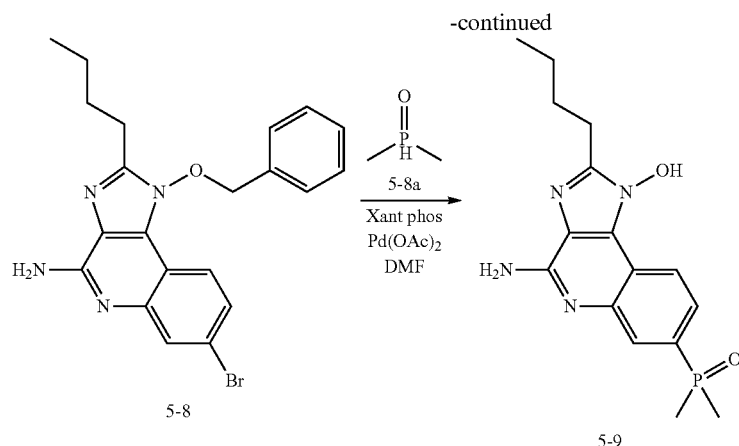
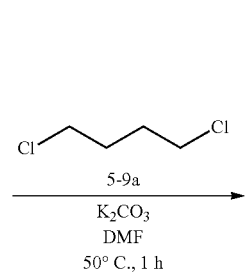
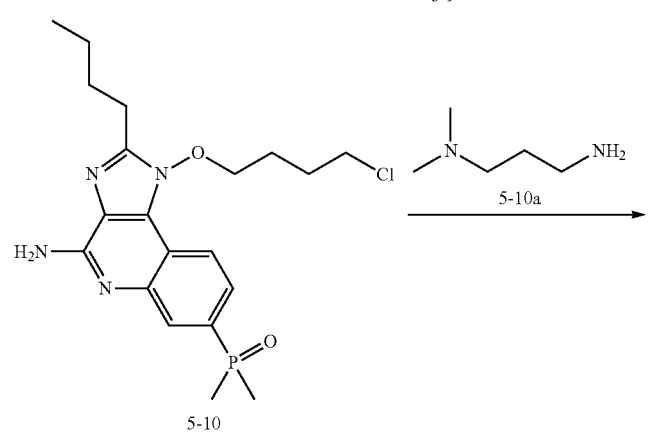
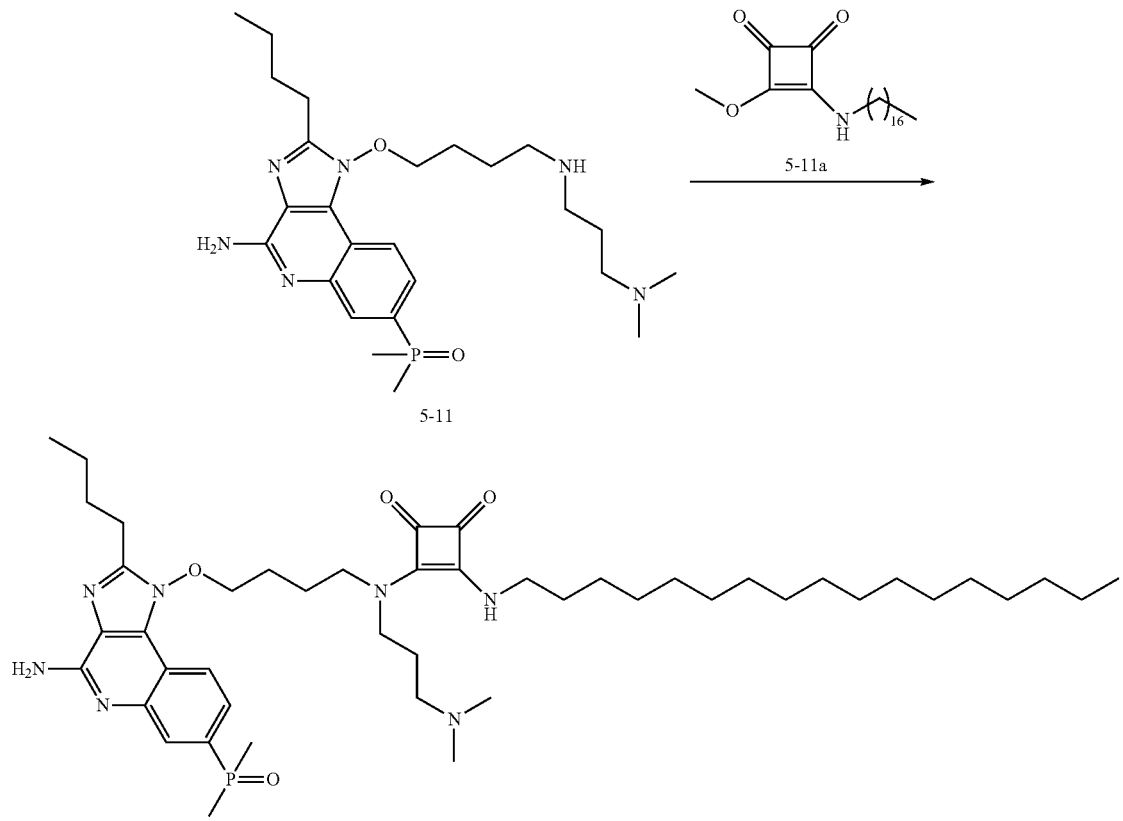

Step 1. To a solution of compound 5-1 (30.0 g, 135 mol) in propionic acid (240 mL) was added nitric acid (15.0 mL, 70%) at rt. The reaction mixture was heated to 130° C. overnight. The reaction mixture was cooled to room temperature and filtered. The resulting solid was washed with water (150 mL×3) and dried in vacuum to give compound 5-2 (25 g, yield: 69.4%) as a yellow solid.

Step 2: To a solution of compound 5-2 (25.0 g, 93.75 mmol) was in $POCl_3$ (70 mL) was added anhydrous DMF (5 mL). The reaction mixture was heated to 85° C. under nitrogen overnight. The reaction mixture was cooled to room temperature. The precipitate was collected by filtration, washed with water and dried in high vacuum to give compound 5-3 (24.0 g, yield: 92%) as a yellow solid.

Step 3: To a solution of compound 5-3 (24 g, 84.0 mmol) in EtOH/THF(5:1) (288 mL) was added $SnCl_2 2H_2O$ (75.9 g. 336 mmol) as one portion. The reaction mixture was then stirred at 70° C. for 3 hours. LCMS showed the mixture was completed, The reaction mixture was cooled to 0° C. and adjusted to pH=8 with saturated $NaHCO_3$. The mixture was extracted with DCM (200 mL×5). The combined organic layers were dried over $Na_2SO_4$, filtered and concentrated in vacuo to give compound 5-4 (17.5 yield: 81.4%) as a yellow solid. NMR (400 MHz, DMSO-d6) δ8.59 (s, 1H), 8.05 (d, 2.0 Hz, 1H), 7.82 (d, J=8.8 Hz, 1H), 7.69 (dd, J=8.8, 2.0 Hz, 1H), 6.22 (s, 2H). LCMS: [mobile phase: 0.1% FA and 10% ACN in $H_2O$ and 0.1% FA and 10% $H_2O$ in ACN in 2.6 min] purity=83.6%, Rt=1.738 mm; MS Calcd.: 255,9, MS m/z (EST): 258.9 $[M+H]^+$.

Step 4: To a solution of compound 5-4 (17.5 g, 68.4 mmol) in pyridine (100 mL) was added pentanoic anhydride (25.4 g, 13.8 mmol) and py.HCl(1.4 g). The reaction mixture was stirred at 50° C. for 1 hour. LCMS showed the mixture was completed. The solvent was evaporated in vacuum. The residue was added PE/EA (5:1)(120 mL) and stirred overnight, filtered to give compound 5-5 (19 g, yield: 82.6%) as a yellow solid. $^1$H NMR (400 MHz. DMSO-d6) δ10.12 (s, 1H), 9.08 (s, 1H), 8.31 (d, J=2.0 Hz, 1H), 8.12 (d, J=9.0 Hz, 1H), 7.90 (dd, J=9.0, 2.0 Hz, 1H), 2.50-2.46 (m, 2H), 1.74-1.53 (m, 2H), 1.39 (dd, J=14.8, 7.2 Hz, 2H), 0.93 (t, J=7.2 Hz, 3H). LCMS: [mobile phase: 0.1% FA and 10% ACN in $H_2O$ and 0.1% FA and 10% $H_2O$ in ACN in 2.6 min] purity=84.7%, Rt=1.766 min; MS Calcd.: 340.0, MS m/z (EST): 342.9 $[M+H]^+$.

Step 5: A solution of compound 5-5 (10.0 g, 29.4 mmol) and compound 5-5a (7.0 g, 44.2 mmol) in isopropyl alcohol (200 mL) was stirred at 80° C. for 2 hours. TLC (PE/EA=2:1) showed the reaction was completed. The reaction mixture was concentrated in vacuo and the residue was purified by column chromatography (PE/EA=2:1) to give compound 5-6 (6.1 g, yield: 50.8%) as a yellow solid, $^1$H NMR (400 MHz, DMSO-d6) δ9.60 (s, 1H), 8.58 (s, 1H), 8.49 (d, J=8.8 Hz, 1H), 8.10 (d, J=8.8 Hz 1H), 7.56-7.44 (m, 5H), 5.51 (s, 2H), 2.82 (t, j=7.6 Hz, 2H), 1.79-1.70 (m, 2H), 1.38 (dd, J=14.8, 7.2 Hz, 2H), 0.91 (t, J=7.2 Hz, 3H).

Step 6: To a solution of 5-6 (4.0 g, 2.44 mmol) in DCM (40 mL) was added 30% $H_2O_2$ (10 mL) and m-CPBA (1.57 g, 7.33 mmol) at 0° C., the reaction mixture was allowed to stirred at 50° C. for 2 hours. LCMS showed most starting material consumed. Sodium carbonate solution (50 mL) added to the mixture, and extracted with DCM (80 mL *2), the combined organic layer was washed brine (100 mL) dried over sodium sulfate, filtered and concentrated in vacuo to give 5-6 (1.0 g, crude) which was used in next step directly. LCMS: [mobile phase: 0.1% FA and 10% ACN in $H_2O$ and 0.1% FA and 10% $H_2O$ in ACN in 2.6 min] purity=69.2%, Rt=1.861. min MS Cald: 425.0, MS m/z (ESI): 426.1 $[M+H]^+$.

Step 7: To a solution of 5-7 (1.0 g, 2.35 mmol) in DCM (30 was added aqueous ammonium hydroxide (1.5 mL) at 0° C., a solution of TosCl (1.12 g, 5.88 mmol) in 10 mL dichloromethane was slowly added with vigorous stirring. The cooling bath was removed and the reaction was stirred for an additional 16 hours. LCMS (MC18-508-042-3) showed the mixture was completed. The mixture, was diluted with sodium carbonate solution (50 mL) and extracted with DCM (100 ml, *2). The combined organic layer was washed with brine (150 mL), dried over sodium sulfate, filtered and concentrated in vacuo. The residue was purified by column chromatography (EA/PE-70%) to afford 5-8 (350 mg, yield: 35%) as a yellow solid. 1H NMR (400 MHz, DMSO-d6) δ8.04 (s, 1H), 7.74 (d, J=2.0 Hz, 1H), 7.51-7.46 (m, 5H), 7.43 (dd, J=8.8. 2.0 Hz, 1H), 6.89 (s, 2H), 5.36 (s, 2H), 2.71-2.64 (m, 2H), 1.67 (dd, J=15.2, 7.6 Hz, 2H). 1.32 (dd, J=14.8, 7.2 Hz, 2H), 0.88 (t, J=7.2 Hz, 3H). LCMS: [mobile phase: 0.1% FA and 10% ACN in $H_2O$ and 0.1% FA and 10% $H_2O$ in ACN in 2.6 min] purity=92.7%, Rt=1.259 min, MS Calcd., 424.0, MS m/z (ESI): 425.1 $[M+H]^+$.

Step 8: To a stirred mixture of compound 5-8 (400 mg, 0.943 mmol) and compound 5-8a (220 mg, 2.83 mmol) in DMF (15 mL) was added. Xantphos (109.0 mg, 0.189 mmol), $Pd(OAc)_2$ (42.2 mg, 0.189 mmol) and $K_3PO_4$ (400 mg, 1.886 mmol). The reaction mixture was stirred at 120° C. for 1.5 hours under $N_2$. LCMS (MC18-508-043) showed the mixture was completed. The reaction mixture was evaporated in vacuum to give compound 5-9 (350 mg, crude), which was used in next step directly. LCMS: [mobile phase: 0.1% FA and 10% ACN in $H_2O$ and 0.1% FA and 10% $H_2O$ in ACN in 2.6 min] purity=75.5%, Rt=0.700 min; MS Calcd.: 332.1, MS m/z: (EST): 333.2 $[M+H]^+$.

Step 9: To a stirred mixture of compound 5-9 (350 mg, 1.05 mmol) and compound 5-9a (340 mg, 2.10 mmol) in DMF (15 mL) was added $K_2CO_3$ (290 mg, 2.10 mmol). The reaction mixture was stirred at 50° C. for 1 hour. The reaction mixture was cooled to rt was evaporated in vacuum and the residue was purified by column chromatography (DCM/MeOH=10:1) to afford 5-10 (220 mg, yield: 50%) as a yellow solid. $^1$H NMR (400 MHz, DMSO-d6) δ8.14 (dd, 8.0, 2.8 Hz, 1H), 7.98 (d, J=13.2 Hz, 1H), 7.63 (t, J=9.2 Hz, 1H), 6.87 (s, 2H), 4.40 (t, J=5.6 Hz, 2H), 3.79 (t-J=5.6 Hz, 2H), 2.97 (t, J=7.6 Hz, 2H), 2.11-1.98 (m, 4H), 1.87-1.80 (m ,2H), 1.72 (s, 3H), 1.69 (s, 3H), 1.45 (dd, J=14.8, 7.2 Hz, 2H), 0.96 (t, J=7.2 Hz, 3H).

Step 10: A solution of compound 5-10 (120 mg, 0.284 mmol) in 5-10a (2 mL) was stirred at 65° C. for 2 hours, LCMS showed 41% product and 29.7% starting material. The mixture was concentrated in vacuo, the residue was purified by prep-HPLC (HCl) to give the desired product 5-11 (40 mg, yield as a light yellow solid. LCMS: [mobile phase: 0.1% FA and 10% ACN in $H_2O$ and 0.1.% FA and 10% $H_2O$ in ACN in 2.6 min] purity=41.3%, Rt=0.342 min; MS Calcd.: 488.3, MS Found: 489.3 $[M+H]^+$.

Step 11: To a solution of 5-11 (40 mg, 0.082 mmol) and 5-11a (62.1 mg, 0.164 mmol) in MeOH (10 mL) was added DIEA (42.3 mg, 0.328 mmol). The mixture was stirred at 30° C. for 16 hours. LCMS showed the reaction was completed. The mixture was concentrated in vacuo, the residue was purified by prep-HPLC (HCl) to give 5 (13.38 mg, yield: 20.0%) as a yellow solid. $^1$H NMR (400 MHz, CD3OD) δ8.51-8.29 (m, 1H), 8.22 (t, J=11.6 Hz, 1H), 8.04-7.88 (m, 1H), 4.66-4.39 (m, 2H), 3.84-3.48 (m, 6H), 3.23-3.18 (m, 2H), 3.10-3.02 (m, 2H), 2.92 (s, 6H), 2.21-2.00 (m, 4H), 1.97-1.88 (m, 8H), 1.83-1.58 (m, 4H), 1.56-1.47 (m, 2H), 1.39-1.15 (m, 28H), 1.02 (t, J=8.4 Hz, 3H), 0.89 (t, J=6.8 Hz, 3H). LCMS: [mobile phase: 0.1% FA and 10% ACN in H$_2$O and 0.1% FA and 10% H$_2$O in ACN 13 min] purity=99.255%, Rt=5.351 min; MS Calcd.: 821.5, MS Found: 822.7 [M+H]$^+$.
Example 6
(4-amino-butyl-1-(4-(4-heptadecyl-1H-1,2,3-triazol-1-yl)butoxy)-1H-imidazo[4,5-c]quinolin-7-yl)dimethylphosphine Oxide (6)
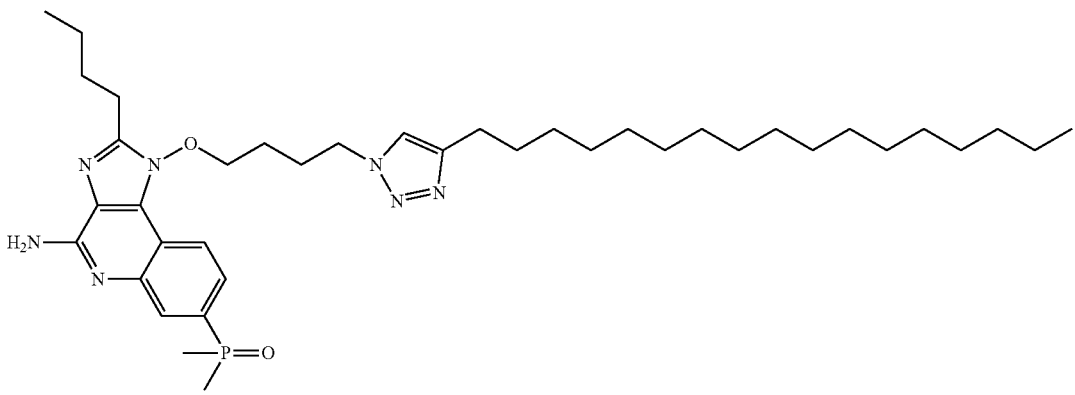
6
Scheme 6
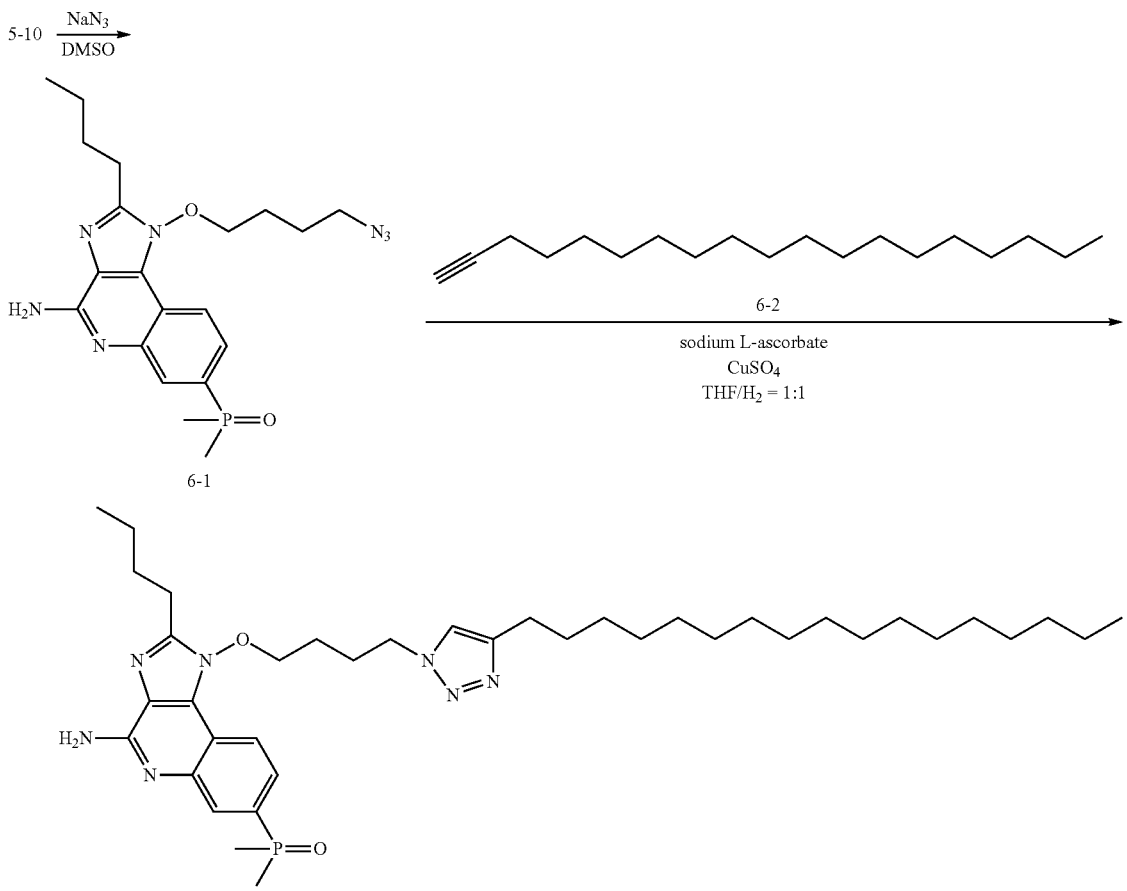
6

Step 1: To a solution of 5-10 (100 mg, 0.237 mmol) in DMSO (5 mL) was added NaN$_3$ (30.8 mg, 0.474 mmol), the mixture was stirred at 80° C. for 1 h. LCMS showed the reaction was completed. The mixture was diluted with water (50 and extracted with EA (20 mL *5). The combined organic layers were dried over sodium sulfate, filtered and concentrated in vacuo to afford 6-1 (70 mg, yield: 68.6%) as a yellow solid. $^1$H NMR (400 MHz, DMSO-d6) 8.13 (dd, J=8.0, 2.8 Hz, 1H) 7.96 (d, J=13.2 Hz, 1H, 7.61 (t, J=9.2 Hz, 1H), 6.80 (s, 2H), 4.38 (t, J=6.4 Hz, 2H), 3.49 (t, J=6.8 Hz, 2H), 2.97 (t, J=7.6 Hz, 2H), 1.97 (dd, J=14.2, 6.4 Hz, 2H), 1.82 (dd, 14.0, 6.8 Hz, 4H), 1.72 (s, 3H), 1.68 (s, 3H), 1.44 (dd, J=14.8, 7.2 Hz, 2H), 0.95 (t, J=7.2 Hz, 3H), LCMS: [mobile phase: 0.1% FA and 10% ACN in H$_2$O and 0.1% FA and 10% H$_2$O in ACN in 2.6 min] purity=86.7%, Rt=1.040 min; MS Calcd.: 429.2, MS m/z (ESI): 430.3 [M+H]$^+$.

Step 2:. To a solution of 6-1 (70 mg, 0.163 mmol) and 6-2 (51.8 mg, 0.196 mmol) in THF/H$_2$O=1.1 (10 mL) were added CuSO$_4$ (5.22 mg, 0.033 mmol) and sodium L-ascorbate (19.4 mg, 0.065 mmol), the mixture was stirred at 40° C. for 2 hours. The mixture was diluted with water (10 mL) and extracted with EA (20 mL *5). The combined organic layer was dried over sodium sulfate, filtered and concentrated in vacuo. The residue was purified b prep-HPLC (HCl) to 6 (28.55 mg, yield 25.3%) as a light yellow solid. $^1$H NMR (400 MHz, CD3OD) δ8.58 (s, 1H), 8.43 (d, J=6.8 Hz, 1H), 8.23 (d, J=12.8 Hz, 1H), 7.99 (t, 9.2 Hz, 1H), 4.78 (t, J=6.8 Hz, 2H), 4.53 (t, J=6.0 Hz, 2H), 3.08 (t, J=7.6 Hz, 2H), 2.90 (t, J=7.6 Hz, 2H), 2.41-2.32 (m, 2H), 2.16-2.11 (m, 2H), 1.99-1.95 (m, 2H), 1.92 (s, 3H), 1.90 (s, 3H), 1.81-1.74 (m, 2H), 1.56-1.50 (m, 2H), 1.42-1.35 (m, 4H), 1.33-1.27 (m, 24H), 1.02 (t, J=7.2 Hz, 3H), 0.88 (t, J=7.2 Hz, 3H). LCMS: [mobile phase: 0.1% FA and 10% ACN in H$_2$O and 0.1% FA and 10% H$_2$O in ACN in 2.6 min] purity=100%, Rt=1.878 min; MS Calcd.: 693.5, MS m/z (ESI): 694.5 [M+H]+.

Example 7

3-(4-(4-amino-2-butyl-7-(diethylphosphoryl)-1H-imidazo[4,5-c]quinolin-yloxy)butylamino)-4-(heptadecylamino)cyclabut-3-ene-1,2- dione (7)

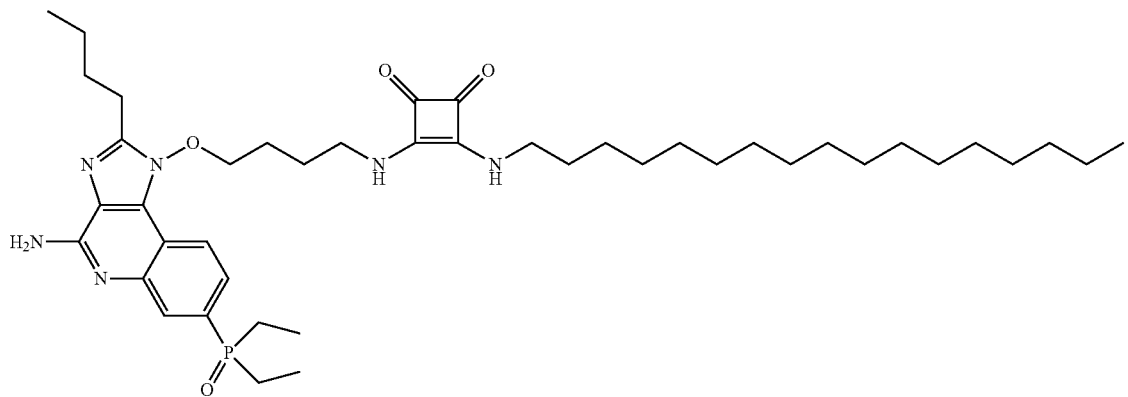

Scheme 7

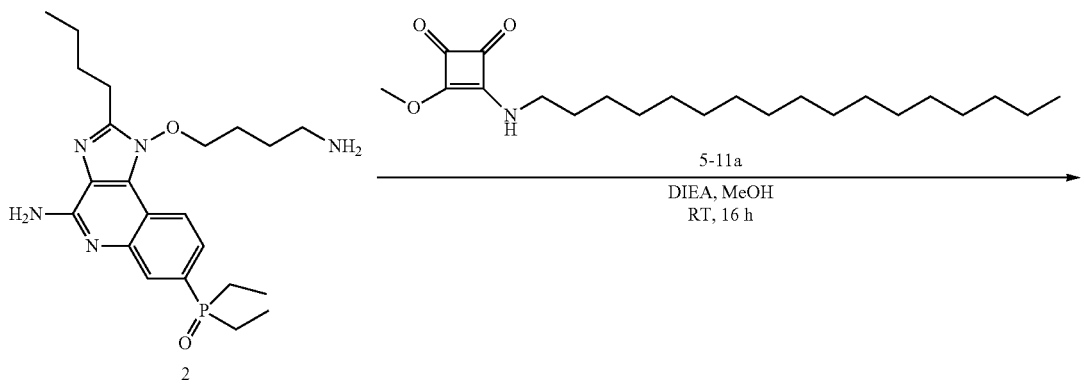

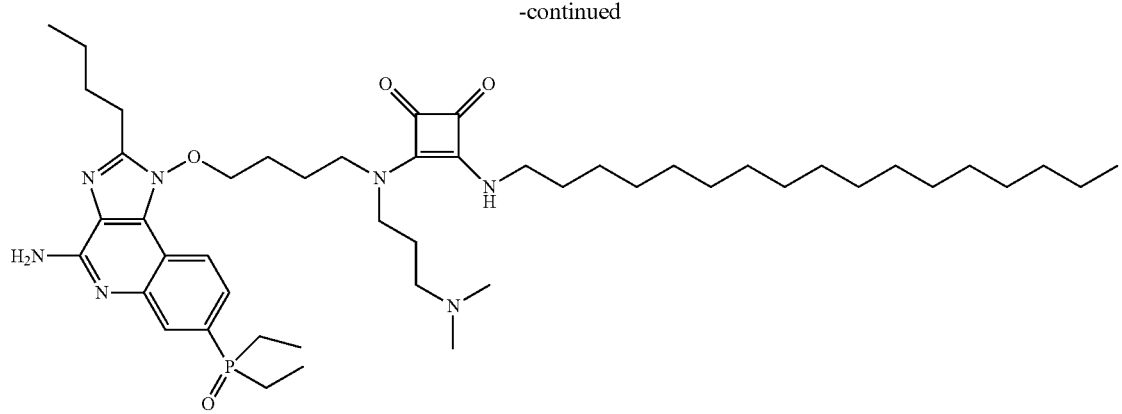

7

To a solution of 2 (10 mg, 0.0232 mmol) and 5-11a (12.7 mg, 0.0348 mmol) ire MeOH (5 mL) was added DIEA (6.0 mg. 0.0464 mmol). The mixture was stirred at room temperature for 16 hours. LCMS showed the reaction was completed. The mixture was concentrated in vacuo, the residue was purified by prep-HPLC (0.02%. HCl) to give 7 as HCl salt (10.5 mg, yield: 59%) as a yellow solid. 1H NMR (400 MHz, MeOD) δ8.44 (dd, 8.2, 2.4 Hz, 1H), 8.21 (d, J=11.6 Hz, 1H), 7.92 (t, J=8.8 Hz, 1H), 4.53 (t, 6.4 Hz, 2H), 3.77 (t, J=6.0 Hz, 2H), 3.62 (br.s, 2H), 3:08 (t, J=7.6 Hz, 2H), 2.29-2.10 (m, 6H), 2.02-1.91 (m, 4H), 1.66-1.59 (m, 2H), 1.55-1.48 (m, 2H), 1.38-1.25 (m, 28H), 1.17-1.09 (m, 6H), 1.02 (t, J=7.4 Hz, 3H), 0.89 (t, J=6.8 Hz, 3H).MS m/z (ESI); 765.7 [M+H]$^+$.

Example 8

TLR7/8 Agonists Induce IFN-Gamma and TNF-Alpha Release in Human PBMC

The system is used to assess the cytokines release. Activity is based on the measurement of interferon-gamma (IFN-γ) and tumor necrosis factor-alpha (TNF-α) secreted into culture media.

Isolation of PBMCs

Fresh human blood was diluted with the same volume of PBS, 15 mL Lymphoprep was added into a Sepmate tube, then 30 mL diluted blood was added on the top gently without disturbing the interface.

The Sepmate tube was centrifuged for 25 min at 1000× a at RT with brake off.

The buffy coat containing peripheral blood mononuclear cells (PBMCs) was collected from Sepmate tube and transferred into a new tube, and the cells were washed with 40 mL PBS twice and centrifuged at 350×g for 5 min.

PBMCs were resuspended in complete culture medium at a density of 2E6/ml.

Compound Preparation

The compounds are solubilized in dimethyl sulfoxide (DMSO) and diluted into indicated concentration with complete culture medium.

The compounds are tested at final concentrations 100 μM, 33.3 μM, 11.1 μM, 3.7 μM, 1.23 μM, 0.41 μM, 0.137 μM, 0.0457 μM and 0.0152 μM.

Incubation

2*10^5 PBMCs (in 100 μl) were added to each well of 96-well flat bottom plate.

2× final concentration of 3-fold serial diluted compounds (in 100 μL) were added to indicated wells and final volume was 200 μL.

The plate was covered with sterile lids, mixed gently and then incubated for 24 h at 37° C./5% $CO_2$ incubator.

Separation Supernatant

Following incubation, the plates was centrifuged for 5 min. at 400×g. The cell-free culture Supernatant was removed into a non-sterile polypropylene plate. Samples are maintained at −80° C. until analysis. The samples were analyzed for TNF-α and IFN-γ by ELISA according to the direction.

TNF-α and IFN-α were analyzed by ELISA. IFN-α concentration was determined by ELISA using a Human IFN-α ELIS Kit from R&D Systems (Catalog #41100-2) and read on VICTOR Nivo™ from PerkinElmer. Results were expressed in pg/mL. TNF-α concentration was determined by ELISA using a Human TNF-alpha ELISA MAX™ Deluxe from BioLegend (Catalog #430205) and read on VICTOR Nivo™ from PerkinElmer. Results were expressed in pg/mL.

The data was analyzed to determine the minimum effective concentration (MEC) for each compound at which induction of a particular cytokine was observed in the assay. Specifically, the MEC of each compound (micromolar) was determined as the lowest concentration of the compound that induced a measured cytokine response at a level (pictograms/mL) that was at least 2× greater than that observed with the negative control wells. The results are presented in Table 2.

TABLE 2

| | MEC to induce cytokine (micromolar) | |
|---|---|---|
| Compound | IFN-alpha | TNF-alpha |
| Example 1 | 0.046 | 3.7 |
| Example 2 | 0.137 | 11.1 |
| Example 3 | 0.015 | 0.015 |
| Example 4 | 1.73 | 11.1 |
| Example 5 | 0.137 | 0.015 |
| Example 6 | >33.3 | >33.3 |
| Example 7 | 0.015 | 3.7 |

Exemplary Pharmaceutical Preparations (A) injection vials: A solution of 100 g of an active ingredient according to the invention and 5 g of disodium hydrogen phosphate in 3 L of distilled water is adjusted to pH 6.5 using 2 N hydrochloric acid, sterile filtered, transferred into injection vials, is lyophilized under sterile conditions and is sealed under sterile conditions Each injection vial contains 5 rag of active ingredient.

(B) Suppositories: A mixture of 20 g of an active ingredient according to the invention is melted with 100 g of soy lecithin and 1400 g of cocoa butter, is poured into moulds and is allowed to cool. Each suppository contains 20 mg of active ingredient.

(C) Solution; A solution is prepared from 1 a of an active ingredient according to the invention, 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 11 and sterilized by irradiation. This solution could be used in the form of eye drops.

(D) Ointment: 500 mg of an active ingredient. according to the invention is mixed with 99.5 g of Vaseline under aseptic conditions.

(E) Tablets: A mixture of 1 kg of an active ingredient according to the invention, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

(F) Coated tablets: Tablets are pressed analogously to Example E and subsequently are coated in a conventional manner with a coating of sucrose, potato starch, talc, tragacanth and dye.

(G) Capsules: 2 kg of an active ingredient according to the invention are introduced into hard gelatin capsules in a conventional manner in such a way that each capsule contains 20 mg of the active ingredient.

(H) Ampoules: A solution of 1 kg of an active ingredient according to the invention in 60 l of bidistilled water is sterile filtered, transferred into ampoules, is lyophilized under sterile conditions and is sealed under sterile conditions. Each ampoule contains 10 mg of active ingredient.

(I) Inhalation spray: 14 g of an active ingredient according to the invention are dissolved in 10 l of isotonic NaCl solution, and the solution is transferred into commercially available spray containers with a pump mechanism. The solution could be sprayed into the mouth or nose. One spray shot (about 0.1 ml) corresponds to a dose of about 0.14 mg.

Applicant's disclosure is described herein in preferred embodiments with reference to the Figures, in which like numbers represent the same or similar elements . . . Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicant's disclosure may be combined in any suitable manner in one or more embodiments . . . In the description, herein, numerous specific details are recited to provide a thorough understanding of embodiments of the invention . . . One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used. in the practice or testing of the present disclosure, the preferred methods and materials are now described. Methods recited herein may be carried out in any order that is logically possible, in addition to a particular order disclosed.

INCORPORATION BY REFERENCE references and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

What is claimed is:

1. A unit dosage form comprising a compound having the structural formula of (I):

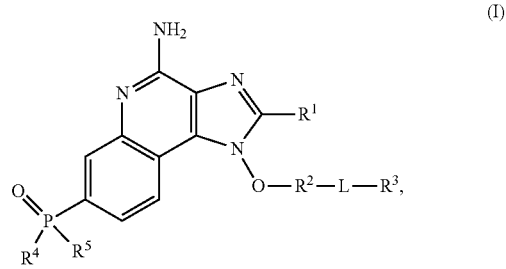

or a pharmaceutically acceptable form or an isotope derivative thereof, wherein, $R^1$ is a $C_1$-$C_8$ alkyl group;

$R^2$ is $(CH_2)_m$, wherein m is an integer selected from 1 to 8;

L is a linking moiety;

$R^3$ is a H, or $C_1$-$C_{32}$ alkyl group; and each of $R^4$ and $R^5$ is independently a $C_1$-$C_6$ aliphatic group; provided that $R^4$ and $R^5$, together with atoms to which they are bonded to, may optionally form a 5- to 7-membered aliphatic ring.

2. The unit dosage of claim 1, wherein each of $R^4$ and $R^5$ is independently a $C_1$-$C_6$ alkyl group.

3. The unit dosage of claim 1, wherein $R^1$ is a $C_3$-$C_6$ alkyl group, m is an integer selected from 3 to 8, and $R^3$ is a H, or a $C_{12}$-$C_{32}$ alkyl group.

4. The unit dosage of claim 3, wherein $R^1$ is a $C_4$ alkyl group, having the structural formula:

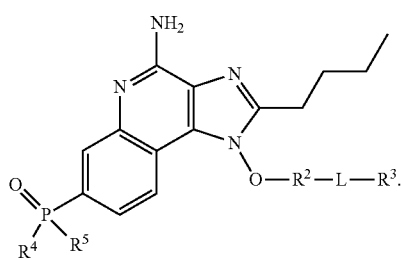

5. The unit dosage of claim 4, having the structural formula:

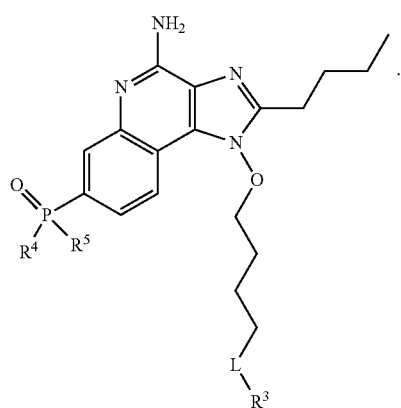

6. The unit dosage of claim 1, wherein L comprises:

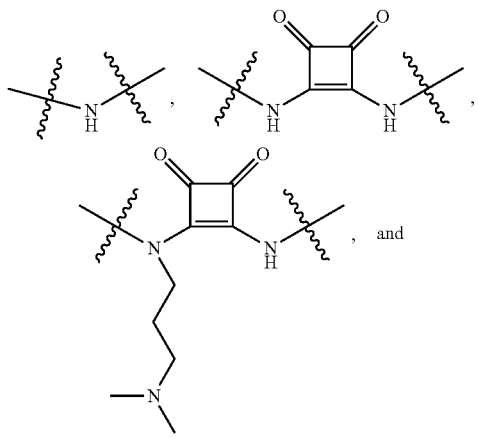

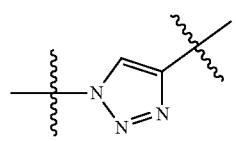

7. A method for treating or reducing a condition or disorder treatable by modulation of TLR7- and/or TLR8-mediated cellular activities, comprising administering to a subject in need thereof a pharmaceutical composition comprising a compound having the structural formula of (I):

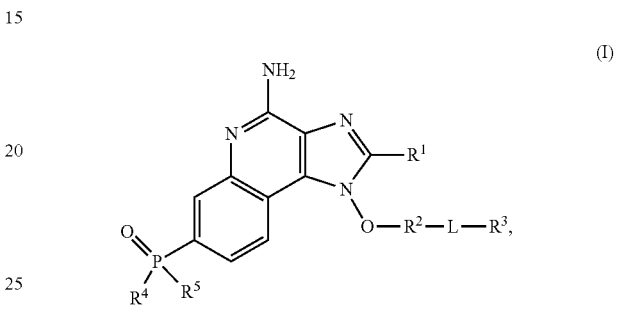

(I)

or a pharmaceutically acceptable form or an isotope derivative thereof, wherein, $R^1$ is a $C_1$-$C_8$ alkyl group;

$R^2$ is $(CH_2)_m$, wherein m is an integer selected from 1 to 8;

L is a linking moiety;

$R^3$ is a H, or $C_1$-$C_{32}$ alkyl group; and each of $R^4$ and $R^5$ is independently a $C_1$-$C_6$ aliphatic group; provided that $R^4$ and $R^5$, together with atoms to which they are bonded to, may optionally form a 5- to 7-membered aliphatic ring.

8. The method of claim 7, wherein the compound is an agonist of TLR7.

9. The method of claim 7, wherein the compound is an agonist of TLR8.

10. The method of claim 7, wherein each of $R^4$ and $R^5$ is independently a $C_1$-$C_6$ alkyl group.

11. The method of claim 7, wherein $R^1$ is a $C_3$-$C_6$ alkyl group, m is an integer selected from 3 to 8, and $R^3$ is a H, or a $C_{12}$-$C_{32}$ alkyl group.

12. The method of claim 11, wherein $R^1$ is a $C_4$ alkyl group, having the structural formula:

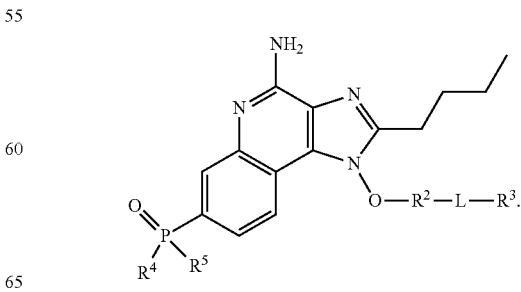

13. The method of claim 12, having the structural formula:
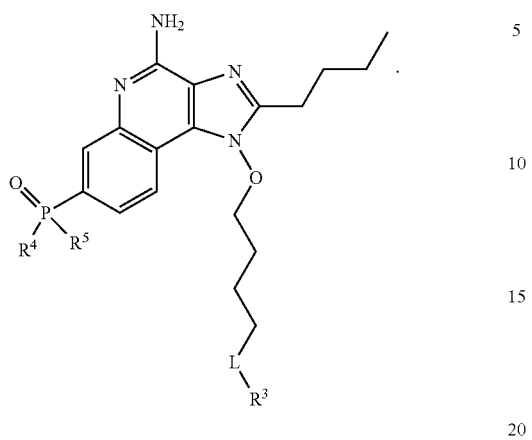
14. The method of claim 7, wherein L comprises:
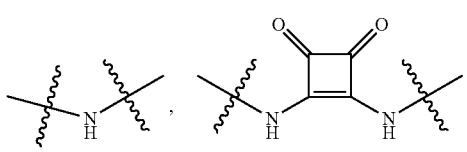
-continued
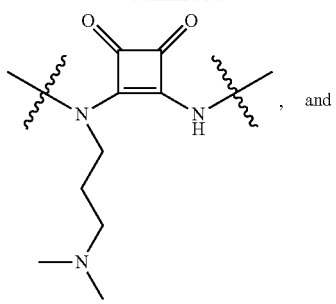, and
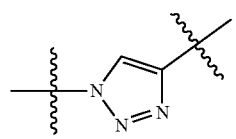.
* * * * *